United States Patent
Chen et al.

(10) Patent No.: US 6,525,102 B1
(45) Date of Patent: Feb. 25, 2003

(54) STABILIZED LIQUID POLYPEPTIDE-CONTAINING PHARMACEUTICAL COMPOSITIONS

(75) Inventors: Bao-Lu Chen, San Ramon, CA (US); Maninder S. Hora, Danville, CA (US)

(73) Assignee: Chiron Corporation, Emeryville, CA (US)

(*) Notice: Subject to any disclaimer, the term of this patent is extended or adjusted under 35 U.S.C. 154(b) by 0 days.

(21) Appl. No.: 09/677,643

(22) Filed: Oct. 3, 2000

Related U.S. Application Data

(60) Provisional application No. 60/157,696, filed on Oct. 4, 1999.

(51) Int. Cl.⁷ .................. A01N 25/00; A61K 39/00; A61K 45/00; A61K 38/21; C07K 17/00
(52) U.S. Cl. .................. 514/970; 424/198.1; 424/85.1; 424/85.2; 424/85.4; 424/85.6
(58) Field of Search .................. 424/85.2, 85.1, 424/85.4, 85.6, 198.1; 514/970, 975; 630/351

(56) References Cited

U.S. PATENT DOCUMENTS

| | | | |
|---|---|---|---|
| 4,650,674 A | * 3/1987 | Aggarwal et al. | 424/85.4 |
| 4,812,557 A | 3/1989 | Yasushi et al. | |
| 4,883,661 A | 11/1989 | Daly et al. | |
| 4,894,226 A | 1/1990 | Aldwin et al. | |
| 4,931,543 A | 6/1990 | Halenbeck et al. | |
| 5,034,225 A | * 7/1991 | Bennett et al. | 424/94.64 |
| 5,078,997 A | 1/1992 | Hora et al. | |
| 5,272,135 A | 12/1993 | Takruri | |
| 5,340,574 A | 8/1994 | Maneglier et al. | |
| 5,358,708 A | 10/1994 | Patel | |
| 5,744,132 A | 4/1998 | Warne et al. | |
| 5,795,779 A | 8/1998 | McCormick et al. | |

FOREIGN PATENT DOCUMENTS

| | | |
|---|---|---|
| EP | 0 229 016 A2 | 7/1987 |
| EP | 0 303 746 A1 | 2/1989 |
| IE | 921124 | 10/1992 |
| WO | WO96/40784 A2 | 12/1996 |
| WO | WO99/51272 A1 | 10/1999 |

OTHER PUBLICATIONS

Allen et al. Int J Pharm 1999 , vol. 187, pp. 259–272. Hybrid (BDBB) interferon–alpha.: preformulation studies.*
Taneja et al. Biochem J. 1994, vo. 303, pp. 147–153. Increased thermal stability of proteins in the presence of amiino acids.*
Heller et al. Biotechnol prog. 1997, vol. 13, pp. 590–596. Manipulation of lypphilization–induced phase seperation: Implications for pharmceutical proteins.*
Wang et al. (1988 Supp.) "Parenteral Formulations of Proteins and Peptides: Stability and Stabilizers," *Journal of Parenteral Science and Technology* 42:S1–S26.
Chang et al. (1996) "Development of a Stable Freeze–dried Formulation of Recombinant Human Interleukin–1 Receptor Antagonist," *Pharmaceutical Research 13*: 243–249.
Chen et al. (1999) "Solubility of Recombinant Human Tissue Factor Pathway Inhibitor," *Journal of Pharmaceutical Sciences 88*: 881–888.

* cited by examiner

*Primary Examiner*—Yvonne Eyler
*Assistant Examiner*—Janet L. Andres
(74) *Attorney, Agent, or Firm*—Robert P. Blackburn; Charlene A. Launer; Leslie T. Henry

(57) ABSTRACT

Stabilized liquid polypeptide-containing pharmaceutical compositions are provided. The compositions comprise an amino acid base, which serves as the primary stabilizing agent of the polypeptide, and an acid and/or its salt form to buffer the solution within an acceptable pH range for stability of the polypeptide. The compositions are near isotonic. Methods for increasing stability of a polypeptide in a liquid pharmaceutical composition and for increasing storage stability of such a pharmaceutical composition are also provided.

58 Claims, 11 Drawing Sheets

STABILIZED LIQUID POLYPEPTIDE-CONTAINING PHARMACEUTICAL COMPOSITIONS

CROSS REFERENCE TO RELATED APPLICATION

This application claims the benefit of U.S. Provisional Application Serial No. 60/157,696, filed Oct. 4, 1999, the contents of which are herein incorporated by reference in their entirety.

FIELD OF THE INVENTION

The present invention relates generally to pharmaceutical compositions, more particularly to pharmaceutical compositions comprising polypeptides that typically are unstable in liquid pharmaceutical formulations.

BACKGROUND OF THE INVENTION

Recent advances in the development of genetic engineering technology have provided a wide variety of biologically active polypeptides in sufficiently large quantities for use as drugs. Polypeptides, however, can lose biological activity as a result of physical instabilities, including denaturation and formation of soluble and insoluble aggregates, and a variety of chemical instabilities, such as hydrolysis, oxidation, and deamidation. Stability of polypeptides in liquid pharmaceutical formulations can be affected, for example, by factors such as pH, ionic strength, temperature, repeated cycles of freeze-thaw, and exposure to mechanical shear forces such as occur during processing. Aggregate formation and loss of biological activity can also occur as a result of physical agitation and interactions of polypeptide molecules in solution and at the liquid-air interfaces within storage vials. Further conformational changes may occur in polypeptides adsorbed to air-liquid and solid-liquid interfaces during compression-extension of the interfaces resulting from agitation during transportation or otherwise. Such agitation can cause the protein to entangle, aggregate, form particles, and ultimately precipitate with other adsorbed proteins. For a general review of stability of protein pharmaceuticals, see, for example, Manning et al. (1989) Pharm. Res. 6:903–918, and Wang and Hanson (1988) J. Parenteral Sci. Tech. 42:S14.

Instability of polypeptide-containing liquid pharmaceutical formulations has prompted packaging of these formulations in the lyophilized form along with a suitable liquid medium for reconstitution. Although lyophilization improves storage stability of the composition, many polypeptides exhibit decreased activity, either during storage in the dried state (Pikal (1990) Biopharm. 27:26–30) or as a result of aggregate formation or loss of catalytic activity upon reconstitution as a liquid formulation (see, for example, Carpenter et al. (1991) Develop. Biol. Standard 74:225–239; Broadhead et al. (1992) Drug Devel. Ind. Pharm. 18:1169–1206; Mumenthaler et al. (1994) Pharm. Res. 11:12–20; Carpenter and Crowe (1988) Cryobiology 25:459–470; and Roser (1991) Biopharm. 4:47–53). While the use of additives has improved the stability of dried proteins, many rehydrated formulations continue to have unacceptable or undesirable amounts of inactive, aggregated protein (see, for example, Townsend and DeLuca (1983) J. Pharm. Sci. 80:63–66; Hora et al. (1992) Pharm. Res. 9:33–36; Yoshiaka et al. (1993) Pharm. Res, 10:687–691). Also, the need for reconstitution is an inconvenience and introduces the possibility of incorrect dosing.

While a number of liquid pharmaceutical compositions have been formulated to stabilize the biological activity of polypeptides contained therein, the degradation of polypeptides in liquid formulations continues to create problems for medical practitioners. Consequently, there is a need for additional pharmaceutical compositions comprising physiologically compatible stabilizers that promote stability of polypeptide components, thereby maintaining their therapeutic effectiveness.

SUMMARY OF THE INVENTION

Compositions comprising a polypeptide as a therapeutically active component and methods useful in their preparation are provided. The compositions are stabilized liquid pharmaceutical compositions that include a polypeptide whose effectiveness as a therapeutically active component is normally compromised during storage in liquid formulations as a result of aggregation of the polypeptide. The stabilized liquid pharmaceutical compositions of the invention comprise, in addition to a polypeptide that exhibits aggregate formation during storage in a liquid formulation, an amount of an amino acid base sufficient to decrease aggregate formation of the polypeptide during storage, where the amino acid base is an amino acid or a combination of amino acids, where any given amino acid is present either in its free base form or in its salt form. The compositions further comprise a buffering agent to maintain pH of the liquid composition within an acceptable range for stability of the polypeptide, where the buffering agent is an acid substantially free of its salt form, an acid in its salt form, or a mixture of an acid and its salt form.

The amino acid base serves to stabilize the polypeptide against aggregate formation during storage of the liquid pharmaceutical composition, while use of an acid substantially free of its salt form, an acid in its salt form, or a mixture of an acid and its salt form as the buffering agent results in a liquid composition having an osmolarity that is nearly isotonic. The liquid pharmaceutical composition may additionally incorporate other stabilizing agents, more particularly methionine, a nonionic surfactant such as polysorbate 80, and EDTA, to further increase stability of the polypeptide. Such liquid pharmaceutical compositions are said to be stabilized, as addition of amino acid base in combination with an acid substantially free of its salt form, an acid in its salt form, or a mixture of an acid and its salt form, results in the compositions having increased storage stability relative to liquid pharmaceutical compositions formulated in the absence of the combination of these two components.

Methods for increasing stability of a polypeptide in a liquid pharmaceutical composition and for increasing storage stability of such a pharmaceutical composition are also provided. The methods comprise incorporating into the liquid pharmaceutical composition an amount of an amino acid base sufficient to decrease aggregate formation of the polypeptide during storage of the composition, and a buffering agent, where the buffering agent is an acid substantially free of its salt form, an acid in its salt form, or a mixture of an acid and its salt form. The methods find use in preparation of the liquid pharmaceutical compositions of the invention.

DETAILED DESCRIPTION OF THE INVENTION

Figure 1:
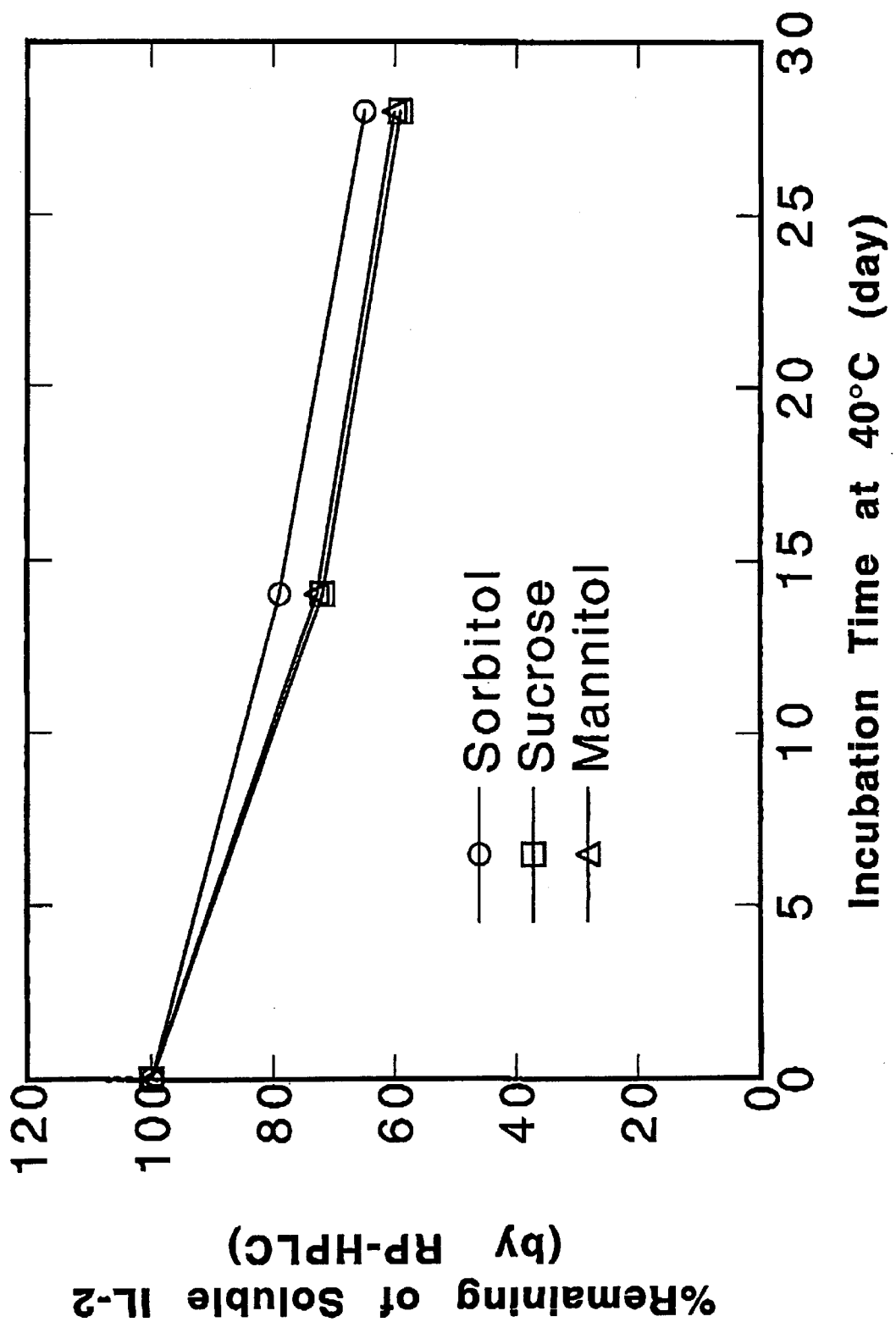
FIG. 1 shows the percent remaining of soluble IL-2 in stability samples stored at 40° C., as analyzed by RP-HPLC. Formulations contained 0.2 mg/ml IL-2, 10 mM sodium succinate at pH 6, and 270 mM sorbitol or sucrose or mannitol.

The present invention is directed to liquid pharmaceutical compositions comprising a polypeptide as a therapeutically active component and to methods useful in their preparation. For purposes of the present invention, the term "liquid" with regard to pharmaceutical compositions or formulations is intended to include the term "aqueous". The term "polypeptide" as used herein encompasses naturally occurring (native), synthetic, and recombinant polypeptides and proteins, and biologically active variants thereof, as qualified elsewhere herein. By "therapeutically active component" is intended the polypeptide is specifically incorporated into the composition to bring about a desired, therapeutic response with regard to treatment, prevention, or diagnosis of a disease or condition within a subject when the pharmaceutical composition is administered to that subject.

More particularly, compositions of the invention are stabilized liquid pharmaceutical compositions whose therapeutically active components include a polypeptide that normally exhibits aggregate formation during storage in liquid pharmaceutical formulations. By "aggregate formation" is intended a physical interaction between the polypeptide molecules that results in formation of oligomers, which may remain soluble, or large visible aggregates that precipitate out of solution. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or formulation is dried either by freeze drying (i.e., lyophilization; see, for example, Williams and Polli (1984) *J. Parenteral Sci. Technol.* 38:48–59), spray drying (see Masters (1991) in *Spray-Drying Handbook* (5th ed; Longman Scientific and Technical, Essez, U.K.), pp. 491–676; Broadhead et al. (1992) *Drug Devel. Ind. Pharm.* 18:1169–1206; and Mumenthaler et al. (1994) *Pharm. Res.* 11:12–20), or air drying (Carpenter and Crowe (1988) *Cryobiology* 25:459–470; and Roser (1991) *Biopharm.* 4:47–53). Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

The stabilized liquid pharmaceutical compositions of the invention further comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. Preferred amino acids to use in preparing the compositions of the invention are those carrying a charged side chain, such as arginine, lysine, aspartic acid, and glutamic acid. Any stereoisomer (i.e., L, D, or DL isomer) of a particular amino acid, or combinations of these stereoisomers, may be present in the pharmaceutical compositions of the invention so long as the particular amino acid is present either in its free base form or its salt form. Preferably the L-stereoisomer is used. Compositions of the invention may also be formulated with analogues of these preferred amino acids. By "amino acid analogue" is intended a derivative of the naturally occurring amino acid that brings about the desired effect of decreasing aggregate formation by the polypeptide during storage of the liquid pharmaceutical compositions of the invention. Suitable arginine analogues include, for example, aminoguanidine and N-monoethyl L-arginine. As with the preferred amino acids, the amino acid analogues are incorporated into the compositions in either their free base form or their salt form.

In combination with the amino acid base as defined herein, the stabilized liquid pharmaceutical compositions of the invention further comprise an acid substantially free of its salt form, an acid in its salt form, or a mixture of an acid and its salt form to maintain solution pH. Preferably, the pH is maintained by using the amino acid base in combination with an acid substantially free of its salt form. Such a combination provides for a lower osmolarity of the solution than if an acid and its salt form are used as buffering agents in combination with an amino acid base to formulate a stabilized pharmaceutical composition. The advantage of such a combination is that one can incorporate a higher concentration of the stabilizer, the amino acid base, into the pharmaceutical composition without exceeding isotonicity of the solution. By "an acid substantially free of its salt form" is intended that the acid serving as the buffering agent within the liquid pharmaceutical composition is present in the absence of any of its salt forms. Typically, when a buffer comprising an acid is used in a liquid pharmaceutical composition, it is prepared using a salt form of the acid or a combination of the acid and a salt form of the acid. Thus, for example, the buffer is prepared using the acid with its counterion, such as sodium, potassium, ammonium, calcium, or magnesium. Hence, a succinate buffer generally consists of a salt of succinic acid, such as sodium succinate, or a mixture of succinic acid and sodium succinate. Although the acid used as a buffering agent in the stabilized liquid pharmaceutical compositions of the invention can be the salt form of the acid or a mixture of the acid and its salt form, preferably the acid serving as a buffering agent is solely in its acid form. Acids suitable for use in formulating the stabilized liquid polypeptide-containing compositions of the present invention include, but are not limited to, succinic acid, citric acid, phosphoric acid, glutamic acid, maleic acid, malic acid, acetic acid, tartaric acid, and aspartic acid, more preferably succinic acid and citric acid, most preferably succinic acid.

The liquid polypeptide-containing pharmaceutical compositions of the invention are "stabilized" compositions. By "stabilized" is intended the liquid compositions have increased storage stability relative to compositions prepared in the absence of the combination of an amino acid base and a buffering agent as disclosed herein. This increased storage stability is observed in the liquid formulation, whether stored directly in that form for later use, stored in a frozen state and thawed prior to use, or prepared in a dried form, such as a lyophilized, air-dried, or spray-dried form, for later reconstitution into a liquid form or other form prior to use. Preferably, compositions of the invention are stored directly in their liquid form to take full advantage of the convenience of having increased storage stability in the liquid form, ease of administration without reconstitution, and ability to supply the formulation in prefilled, ready-to-use syringes or as multidose preparations if the formulation is compatible with bacteriostatic agents.

The compositions of the invention relate to the discovery that the addition of the amino acid arginine, lysine, aspartic acid, or glutamic acid in its free base form or in its salt form in combination with an acid substantially free of its salt form, an acid in its salt form, or a mixture of an acid and its salt form, results in a liquid polypeptide-containing pharmaceutical composition that has increased storage stability relative to a liquid polypeptide-containing pharmaceutical composition prepared without the combination of these two components. The increased storage stability of the composition is achieved through the influence of the amino acid on stability of the therapeutically active polypeptide, more particularly its influence on polypeptide aggregation during storage in liquid formulations. Furthermore, incorporation of an amino acid base as defined herein and an acid substantially free of its salt form within liquid polypeptide-containing formulations results in liquid pharmaceutical compositions that are near isotonic without having to include additional isotonizing agents, such as sodium chloride. By "near isotonic" is intended the liquid composition has an osmolarity of about 240 mmol/kg to about 360 mmol/kg, preferably about 240 to about 340 mmol/kg, more preferably about 250 to about 330 mmol/kg, even more preferably about 260 to about 320 mmol/kg, most preferably about 270 to about 310 mmol/kg.

The amino acid base incorporated into the stabilized liquid pharmaceutical compositions of the invention protects the therapeutically active polypeptide against aggregation, thereby increasing stability of the polypeptide during storage of the composition. By "increasing stability" is intended that aggregate formation by the polypeptide during storage of the liquid pharmaceutical composition is decreased relative to aggregate formation of the polypeptide during storage in the absence of this particular stabilizing agent. Decreased aggregate formation with addition of amino acid base occurs in a concentration dependent manner. That is, increasing concentrations of amino acid base lead to increased stability of a polypeptide in a liquid pharmaceutical composition when that polypeptide normally exhibits aggregate formation during storage in a liquid formulation in the absence of the amino acid base. Determination of the amount of a particular amino acid base to be added to a liquid pharmaceutical composition to decrease aggregate formation thereby increasing polypeptide stability, and thus increasing storage stability of the composition, can readily be determined for any particular polypeptide of interest without undue experimentation using methods generally known to one of skill in the art.

Thus, for example, the effect of a particular amino acid base on polypeptide aggregation during storage in a liquid composition can be readily determined by measuring the change in soluble polypeptide in solution over time. Amount of soluble polypeptide in solution can be quantified by a number of analytical assays adapted to detection of the polypeptide of interest. Such assays include, for example, reverse phase (RP)-HPLC, size exclusion (SEC)-HPLC, and UV absorbance, as described in the Examples below. Where a polypeptide of interest forms both soluble and insoluble aggregates during storage in liquid formulations, a combination of RP-HPLC and SEC-HPLC can be used to distinguish between that portion of the soluble polypeptide that is present as soluble aggregates and that portion that is present in the nonaggregate, biologically active molecular form, as described in Example 1 below.

In the case of aggregation, an effective amount of amino acid base to incorporate within a polypeptide-containing liquid pharmaceutical composition to obtain the stabilized pharmaceutical composition of the invention would be viewed as an amount that resulted in decreased aggregate formation over time, and hence greater retention of soluble polypeptide in solution in its nonaggregated, biologically active molecular form. Thus, for example, where the polypeptide is a monomeric protein, such as the interleukin-2 (IL-2) or tissue factor pathway inhibitor (TFPI) described in the Examples below, an effective amount of stabilizing agent for use in preparing a stabilized composition of the invention would be an amount that resulted in greater retention of IL-2 or TFPI in its monomeric molecular form.

Increased storage stability of the stabilized liquid polypeptide-containing compositions of the invention may also be associated with the inhibitory effects of the amino acid base on deamidation of glutamine and/or asparagine residues within the therapeutically active polypeptide during storage. The effect of a particular amino acid base on deamidation of these residues during storage in a liquid composition can readily be determined by monitoring the amount of polypeptide present in its deamidated form over time. Methods for measuring molecular species, i.e., native or deamidated, of a articular polypeptide present in solution phase are generally known in the art. Such methods include chromatographic separation of the molecular species and identification using polypeptide molecular weight standards, such as with RP-HPLC as described in the Examples below.

Use of the novel combination of an amino acid base buffered by an acid substantially free of its salt form to increase polypeptide stability within the stabilized liquid pharmaceutical compositions of the invention provides advantages over, for example, the use of an amino acid in a succinic acid/sodium succinate buffer system. This novel combination allows for preparation of near isotonic formulations having higher concentrations of the stabilizing amino acid than can be achieved with the use of a buffer system that is a mixture of an acid and its salt form. The higher concentration of the stabilizing amino acid allows for even greater increases in polypeptide stability, and thus increased storage stability of the formulation.

For example, when succinic acid is used to buffer arginine base added to a liquid formulation comprising the protein interleukin-2 (IL-2) and having a pH optimum for that protein (pH 5.8), the concentration of arginine can be increased to 230 mM while still maintaining isotonicity of the formulation. This results in a doubling of IL-2 storage shelf life at 50° C., which is a measure of protein stability. Although a similar IL-2 storage shelf life can be achieved using the same arginine concentration and succinic acid/sodium succinate as the buffering agent, arginine must be added in its acidic form to achieve a similar pH, and the resulting formulation is hypertonic (see Example 1, Table 1).

Similarly, when citric acid is used to buffer arginine base added to a liquid formulation comprising the protein tissue factor pathway inhibitor (TFPI) and having a pH suitable for that protein (pH 5.5), the concentration of arginine can be increased to 300 mM while still maintaining isotonicity of the formulation. This results in nearly a 50% increase in TFPI storage shelf life at 50° C. Although a similar TFPI storage shelf life can be achieved using the same arginine concentration and citric acid/sodium citrate as the buffering agent, arginine must again be added in its acidic form to achieve a similar pH, and the resulting formulation is hypertonic (see Example 8, Table 18). The ability to use higher concentrations of an amino acid as the primary stabilizing agent eliminates the need for more traditional polypeptide stabilizers such as bovine serum albumin or human serum albumin, which are less desirable stabilizing agents because of potential viral contamination.

In addition, isotonicity of liquid pharmaceutical compositions is desirable as it results in reduced pain upon administration and minimizes potential hemolytic effects associated with hypertonic or hypotonic compositions. Thus, the stabilized compositions of the invention not only have increased storage stability, but also have the added benefit of substantially reduced pain upon administration when compared with formulations using other more traditional buffer systems consisting of an acid and a salt form of the acid. For example, in one embodiment of the invention, the stabilized liquid pharmaceutical composition when injected exhibits reduced pain associated with burning and stinging relative to injection of normal saline (see Example 7).

Having identified the advantages of preparing liquid polypeptide compositions of the invention with an amino acid base as the primary stabilizing agent and an acid substantially free of its salt form as the buffering agent, it is within skill in the art to determine, without undue experimentation, preferred concentrations of each of these components to be incorporated into a liquid pharmaceutical composition comprising a therapeutically active polypeptide of interest that exhibits aggregate formation as described herein to achieve increased polypeptide stability during storage of that composition. Following the protocols disclosed, for example, in Example 1 below, the skilled artisan may assess a range of desired concentrations of the amino acid base and the various buffering acids for use in the liquid pharmaceutical compositions described herein. Preferably the amount of amino acid base incorporated into the composition is within a concentration range of about 100 mM to about 400 mM, preferably about 130 mM to about 375 mM, more preferably about 150 mM to about 350 mM, even more preferably about 175 mM to about 325 mM, still more preferably about 180 mM to about 300 mM, even more preferably about 190 mM to about 280 mM, most preferably about 200 mM to about 260 mM, depending upon the protein present in the composition. Although the buffering agent may be the acid in its salt form, or a mixture of the acid and its salt form, preferably the buffering agent is the acid substantially free of its salt form, for the advantageous reasons disclosed herein. The acid used as the buffering agent is preferably added within a concentration range of about 40 mM to about 250 mM, about 50 mM to about 240 mM, about 60 mM to about 230 mM, about 70 mM to about 220 mM, more preferably about 80 mM to about 210 mM, most preferably about 90 mM to about 200 mM, depending upon the acid used as the buffering agent and the pH optimum for the polypeptide being stabilized against aggregate formation.

In one embodiment, the amino acid base is arginine base present at a concentration of about 230 mM and the acid used as the buffering agent is succinic acid at a concentration of about 128 mM. This allows for the preparation of a liquid polypeptide-containing pharmaceutical composition having an osmolarity that is near isotonic and a pH of about 5.8. In another embodiment, the amino acid base is arginine base present at a concentration of about 300 mM and the acid used as the buffering agent is citric acid at a concentration of about 120 mM. This allows for the preparation of a liquid polypeptide-containing pharmaceutical composition having an osmolarity that is near isotonic and a pH of about 5.5. In yet another embodiment, the amino acid base is arginine base present at a concentration of about 200 mM to about 300 mM and the acid used as the buffering agent is succinic acid at a concentration of about 120 MM to about 180 mM. This allows for the preparation of a liquid polypeptide-containing pharmaceutical composition having an osmolarity of about 256 mmol/kg to about 363 mmol/kg and a pH of about 5.5.

Thus, in another embodiment of the invention, the stabilized liquid pharmaceutical composition comprises IL-2 or variant thereof as the polypeptide, arginine base at a concentration of about 150 mM to about 350 mM, and succinic acid at a concentration of about 80 mM to about 190 mM. In a preferred embodiment, the arginine base is present in the IL-2 liquid pharmaceutical composition at a concentration of about 230 mM and succinic acid is present at a concentration of about 128 mM. This preferred IL-2 composition has a pH of about 5.8 and an osmolarity of about 250 mmol/kg to about 330 mmol/kg. The concentration of IL-2 or variant thereof in these compositions is about 0.01 mg/ml to about 2.0 mg/ml, preferably about 0.02 mg/ml to about 1.0 mg/ml, more preferably about 0.03 mg/ml to about 0.8 mg/ml, most preferably about 0.03 mg/ml to about 0.5 mg/ml.

In yet another embodiment of the invention, the stabilized liquid pharmaceutical composition comprises TFPI or variant thereof as the polypeptide, arginine base at a concentration of about 100 mM to about 400 mM, and succinic acid at a concentration of about 80 mM to about 190 mM. In a preferred embodiment, the arginine base is present in the TFPI liquid pharmaceutical composition at a concentration of about 200 mM to about 300 mM and succinic acid is present at a concentration of about 120 mM to about 180 mM. This preferred TFPI composition has a pH of about 5.5 and an osmolarity of about 240 mmol/kg to about 360 mmol/kg. The concentration of TFPI or variant thereof in these compositions is about 0.01 mg/ml to about 5.0 mg/ml, preferably about 0.05 mg/ml to about 2.0 mg/ml, more preferably about 0.10 mg/ml to about 1.0 mg/ml, most preferably about 0.10 mg/ml to about 0.60 mg/ml.

In another embodiment of the invention, the stabilized liquid pharmaceutical composition comprises TFPI or variant thereof as the polypeptide, arginine base at a concentration of about 175 mM to about 400, and citric acid at a concentration of about 40 mM to about 200 mM. In a preferred embodiment, the arginine base is present in the TFPI liquid pharmaceutical composition at a concentration of about 250 mM to about 350 mM and citric acid is present at a concentration of about 100 mM to about 150 mM. This preferred TFPI composition has a pH of about 5.0–6.5 and an osmolarity of about 240 mmol/kg to about 360 mmol/kg. In yet another embodiment, the arginine base is present at a concentration of about 300 mM and citric acid is present at a concentration of about 120 mM. This TFPI composition has a pH of about 5.5 and an osmolarity of about 240 mmol/kg to about 360 mmol/kg. The concentration of TFPI or variant thereof in these compositions is about 0.01 mg/ml to about 5.0 mg/ml, preferably about 0.05 mg/ml to about 2.0 mg/ml, more preferably about 0.10 mg/ml to about 1.0 mg/ml, most preferably about 0.10 mg/ml to about 0.60 mg/ml.

As shown in the examples below, pH of a liquid polypeptide-containing pharmaceutical formulation affects the stability of the polypeptide contained therein, primarily through its affect on polypeptide aggregate formation. Thus the amount of buffering acid present in the pharmaceutical compositions of the invention will vary depending upon the pH optimum for stability of a particular polypeptide of interest. Determination of this pH optimum can be achieved using methods generally available in the art, and further illustrated in the Examples described herein. Preferred pH ranges for the compositions of the invention are about pH 4.0 to about pH 9.0, more particularly about pH 5.0 to about 6.5, depending upon the polypeptide. Thus, in one embodiment, the pH is about 5.8, more particularly when the polypeptide is IL-2 or variant thereof. In another embodiment, the pH is about 5.5, more particularly when the polypeptide is TFPI or variant thereof.

The stabilized pharmaceutical compositions comprising an amino acid base buffered with an acid substantially free of its salt form, the salt form of the acid, or a mixture of the acid and its salt form, may also comprise additional stabilizing agents, which further enhance stability of a therapeutically active polypeptide therein. Stabilizing agents of particular interest to the present invention include, but are not limited to, methionine and EDTA, which protect the polypeptide against methionine oxidation, and a nonionic surfactant, which protects the polypeptide against aggregation associated with freeze-thawing or mechanical shearing.

In this manner, the amino acid methionine may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L, D, or DL isomer) or combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1:1 to about 1000:1, most preferably 10:1 to about 100:1.

The preferred amount of methionine to be added can readily be determined empirically by preparing the composition comprising the polypeptide of interest with different concentrations of methionine and determining the relative effect on formation of oxidative species of the polypeptide using, for instance, chromatographic separation of the molecular species and identification using polypeptide molecular weight standards, such as with RP-HPLC, as described below in Example 2. That concentration of methionine that maximizes inhibition of oxidation of methionine residues, without having adverse affects on amino acid-related inhibition of polypeptide aggregation, would represent a preferred amount of methionine to be added to the composition to further improve polypeptide stability.

Polypeptide degradation due to freeze thawing or mechanical shearing during processing of the liquid composition of the present invention can be inhibited by incorporation of surfactants into the liquid polypeptide-containing compositions of the invention in order to lower the surface tension at the solution-air interface. Typical surfactants employed are nonionic surfactants, including polyoxyethylene sorbitol esters such as polysorbate 80 (Tween 80) and polysorbate 20 (Tween 20);

polyoxypropylene-polyoxyethylene esters such as Pluronic F68; polyoxyethylene alcohols such as Brij 35; simethicone; polyethylene glycol such as PEG400; lysophosphatidylcholine; and polyoxyethylene-p-t-octylphenol such as Triton X-100. Classic stabilization of pharmaceuticals by surfactants or emulsifiers is described, for example, in Levine et al.(1991) *J. Parenteral Sci. Technol.* 45(3):160–165, herein by reference. A preferred surfactant employed in the practice of the present invention is polysorbate 80.

In addition to those agents disclosed above, other stabilizing agents, such as albumin, ethylenediaminetetracetic acid (EDTA) or one of its salts such as disodium EDTA, can be added to further enhance the stability of the liquid pharmaceutical compositions. The amount of albumin can be added at concentrations of about 1.0% w/v or less. The EDTA acts as a scavenger of metal ions known to catalyze many oxidation reactions, thus providing an additional stabilizing agent.

In one embodiment of the invention, the stabilized liquid pharmaceutical composition comprises IL-2 or variant thereof as the polypeptide, arginine base at a concentration of about 150 mM to about 350 mM, succinic acid at a concentration of about 80 mM to about 190 mM, methionine at a concentration of about 0.5 mM to about 10 mM, EDTA at about 0.1 to about 5.0 mM, and polysorbate 80 at about 0.001% to about 0.2%. In a preferred embodiment, the arginine base is present in this IL-2 liquid pharmaceutical composition at a concentration of about 230 mM and succinic acid is present at a concentration of about 128 mM. This preferred IL-2 composition has a pH of about 5.8 and an osmolarity of about 250 mmol/kg to about 330 mmol/kg. The concentration of IL-2 or variant thereof in these compositions is about 0.01 mg/ml to about 2.0 mg/ml, preferably about 0.02 mg/ml to about 1.0 mg/ml, more preferably about 0.03 mg/ml to about 0.8 mg/ml, most preferably about 0.03 mg/ml to about 0.5 mg/ml.

Where desirable, sugars or sugar alcohols may also be included in the stabilized liquid polypeptide-containing pharmaceutical compositions of the present invention. Any sugar such as mono-, di-, or polysaccharides, or water-soluble glucans, including for example fructose, glucose, mannose, sorbose, xylose, maltose, lactose, sucrose, dextran, pullulan, dextrin, cyclodextrin, soluble starch, hydroxyethyl starch and carboxymethylcellulose-Na may be used. Sucrose is the most preferred sugar additive. Sugar alcohol is defined as a C4–C8 hydrocarbon having an —OH group and includes, for example, mannitol, sorbitol, inositol, galacititol, dulcitol, xylitol, and arabitolm with mannitol being the most preferred sugar alcohol additive. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. Preferably, the sugar or sugar alcohol concentration is between about 1.0 w/v % and about 15.0 w/v %, more preferably between about 2.0 w/v % and about 10.0 w/v %.

The stabilized liquid pharmaceutical compositions of the invention may contain other compounds that increase the effectiveness or promote the desirable qualities of the polypeptide of interest that serves as a therapeutically active component so long as the primary stabilizing effect achieved with the amino acid base is not adversely affected. The composition must be safe for administration via the route that is chosen, it must it must be sterile, and must retain its desired therapeutic activity.

Compositions of the present invention are preferably prepared by premixing the stabilizing and buffering agents, and any other excipients prior to incorporation of the polypeptide of interest. Any additional excipients that may be added to further stabilize the compositions of the present invention must not adversely affect the stabilizing effects of the primary stabilizing agent, i.e., an amino acid base, in combination with the buffering agent, i.e., an acid substantially free of its salt form, the salt form of the acid, or a mixture of the acid and its salt form, as used to obtain the novel compositions disclosed herein. Following addition of a preferred amount of an amino acid base to achieve decreased aggregate formation of a polypeptide of interest, pH of the liquid composition is adjusted using the buffering agent, preferably within a range disclosed herein, more preferably to the pH optimum for the polypeptide of interest. Although pH can be adjusted following addition of the polypeptide of interest into the composition, preferably it is adjusted prior to addition of this polypeptide, as this can reduce the risk of denaturation the polypeptide. Appropriate mechanical devices are then used for achieving a proper mix of constituents.

While specific embodiments of the invention are directed to stabilized compositions comprising interleukin-2 (IL-2) or variant thereof, or tissue factor pathway inhibitor (TFPI) or variant thereof, examples of proteins that are particularly susceptible to degradation via aggregate formation, the utility of the invention extends generally to any pharmaceutical composition containing a polypeptide or variant thereof that exhibits aggregate formation during storage in a liquid formulation. Thus polypeptides suitable for use in the practice of the present invention include, for example, interleukins (e.g., IL-2), interferons including β-interferon (IFN-β) and its muteins such as IFN-$β_{ser17}$ (as described in European Patent Application No. 185459B1 and U.S. Pat. No. 4,588, 585, incorporated herein by reference), tissue factor pathway inhibitor (TFPI), human growth hormone (hGH), insulin, and other like polypeptides that exhibit aggregate formation in a liquid formulation, as well as any biologically active variants thereof.

The polypeptides present in the stabilized liquid pharmaceutical compositions of the invention may be native or obtained by recombinant techniques, and may be from any source, including mammalian sources such as, e.g., mouse, rat, rabbit, primate, pig, and human, provided they meet the criterion specified herein, that is, provided they form aggregates during storage in liquid formulations. Preferably such polypeptides are derived from a human source, and more preferably are recombinant, human proteins from microbial hosts.

Biologically active variants of a polypeptide of interest that serves as a therapeutically active component in the pharmaceutical compositions of the invention are also encompassed by the term "polypeptide" as used herein. Such variants should retain the desired biological activity of the native polypeptide such that the pharmaceutical composition comprising the variant polypeptide has the same therapeutic effect as the pharmaceutical composition comprising the native polypeptide when administered to a subject. That is, the variant polypeptide will serve as a therapeutically active component in the pharmaceutical composition in a manner similar to that observed for the native polypeptide. Methods are available in the art for determining whether a variant polypeptide retains the desired biological activity, and hence serves as a therapeutically active component in the pharmaceutical composition. Biological activity can be measured using assays specifically designed for measuring activity of the native polypeptide or protein, including assays described in the present invention.

Additionally, antibodies raised against a biologically active native polypeptide can be tested for their ability to bind to the variant polypeptide, where effective binding is indicative of a polypeptide having a conformation similar to that of the native polypeptide.

Suitable biologically active variants of a native or naturally occurring polypeptide of interest can be fragments, analogues, and derivatives of that polypeptide. By "fragment" is intended a polypeptide consisting of only a part of the intact polypeptide sequence and structure, and can be a C-terminal deletion or N-terminal deletion of the native polypeptide. By "analogue" is intended an analogue of either the native polypeptide or of a fragment of the native polypeptide, where the analogue comprises a native polypeptide sequence and structure having one or more amino acid substitutions, insertions, or deletions. "Muteins", such as those described herein, and peptides having one or more peptoids (peptide mimics) are also encompassed by the term analogue (see International Publication No. WO 91/04282). By "derivative" is intended any suitable modification of the native polypeptide of interest, of a fragment of the native polypeptide, or of their respective analogues, such as glycosylation, phosphorylation, or other addition of foreign moieties, so long as the desired biological activity of the native polypeptide is retained. Methods for making polypeptide fragments, analogues, and derivatives are generally available in the art.

For example, amino acid sequence variants of the polypeptide can be prepared by mutations in the cloned DNA sequence encoding the native polypeptide of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488–492; Kunkel et al. (1987) *Methods Enzymol.* 154:367–382; Sambrook et al. (1989) *Molecular Cloning: A Laboratory Manual* (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in *Atlas of Protein Sequence and Structure* (Natl. Biomed. Res. Found., Washington, D.C.), herein incorporated by reference. Conservative substitutions, such as exchanging one amino acid with another having similar properties, may be preferred. Examples of conservative substitutions include, but are not limited to, Gly⇔Ala, Val⇔Ile⇔Leu, Asp⇔Glu, Lys⇔Arg, Asn⇔Gln, and Phe⇔Trp⇔Tyr.

In constructing variants of the polypeptide of interest, modifications are made such that variants continue to possess the desired activity. Obviously, any mutations made in the DNA encoding the variant polypeptide must not place the sequence out of reading frame and preferably will not create complementary regions that could produce secondary mRNA structure. See EP Patent Application Publication No. 75,444.

Biologically active variants of a polypeptide of interest will generally have at least 70%, preferably at least 80%, more preferably about 90% to 95% or more, and most preferably about 98% or more amino acid sequence identity to the amino acid sequence of the reference polypeptide molecule, which serves as the basis for comparison. A biologically active variant of a native polypeptide of interest may differ from the native polypeptide by as few as 1–15 amino acids, as few as 1–10, such as 6–10, as few as 5, as few as 4, 3, 2, or even 1 amino acid residue. By "sequence identity" is intended the same amino acid residues are found within the variant polypeptide and the polypeptide molecule that serves as a reference when a specified, contiguous segment of the amino acid sequence of the variant is aligned and compared to the amino acid sequence of the reference molecule. The percentage sequence identity between two amino acid sequences is calculated by determining the number of positions at which the identical amino acid residue occurs in both sequences to yield the number of matched positions, dividing the number of matched positions by the total number of positions in the segment undergoing comparison to the reference molecule, and multiplying the result by 100 to yield the percentage of sequence identity.

For purposes of optimal alignment of the two sequences, the contiguous segment of the amino acid sequence of the variant may have additional amino acid residues or deleted amino acid residues with respect to the amino acid sequence of the reference molecule. The contiguous segment used for comparison to the reference amino acid sequence will comprise at least twenty (20) contiguous amino acid residues, and may be 30, 40, 50, 100, or more residues. Corrections for increased sequence identity associated with inclusion of gaps in the variant's amino acid sequence can be made by assigning gap penalties. Methods of sequence alignment are well known in the art for both amino acid sequences and for the nucleotide sequences encoding amino acid sequences.

Thus, the determination of percent identity between any two sequences can be accomplished using a mathematical algorithm. One preferred, non-limiting example of a mathematical algorithm utilized for the comparison of sequences is the algorithm of Myers and Miller (1988) *CABIOS* 4:11–17. Such an algorithm is utilized in the ALIGN program (version 2.0), which is part of the GCG sequence alignment software package. A PAM120 weight residue table, a gap length penalty of 12, and a gap penalty of 4 can be used with the ALIGN program when comparing amino acid sequences. Another preferred, nonlimiting example of a mathematical algorithm for use in comparing two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873–5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to a nucleotide sequence encoding the polypeptide of interest. BLAST protein searches can be performed with the XBLAST program, score=50, wordlength=3, to obtain amino acid sequences homologous to the polypeptide of interest. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST) can be used. See http://www.ncbi.nlm.nih.gov. Also see the ALIGN program (Dayhoff (1978) in *Atlas of Protein Sequence and Structure* 5:Suppl. 3 (National Biomedical Research Foundation, Washington, D.C.) and programs in the Wisconsin Sequence Analysis Package, Version 8 (available from Genetics Computer Group, Madison, Wis.), for example, the GAP program, where default parameters of the programs are utilized.

When considering percentage of amino acid sequence identity, some amino acid residue positions may differ as a result of conservative amino acid substitutions, which do not affect properties of protein function. In these instances, percent sequence identity may be adjusted upwards to account for the similarity in conservatively substituted amino acids. Such adjustments are well known in the art. See, for example, Myers and Miller (1988) *Computer Applic. Biol. Sci.* 4:11–17.

The precise chemical structure of a polypeptide depends on a number of factors. As ionizable amino and carboxyl groups are present in the molecule, a particular polypeptide may be obtained as an acidic or basic salt, or in neutral form. All such preparations that retain their biological activity when placed in suitable environmental conditions are included in the definition of polypeptides as used herein. Further, the primary amino acid sequence of the polypeptide may be augmented by derivatization using sugar moieties (glycosylation) or by other supplementary molecules such as lipids, phosphate, acetyl groups and the like. It may also be augmented by conjugation with saccharides. Certain aspects of such augmentation are accomplished through post-translational processing systems of the producing host; other such modifications may be introduced in vitro. In any event, such modifications are included in the definition of polypeptide used herein so long as the activity of the polypeptide is not destroyed. It is expected that such modifications may quantitatively or qualitatively affect the activity, either by enhancing or diminishing the activity of the polypeptide, in the various assays. Further, individual amino acid residues in the chain may be modified by oxidation, reduction, or other derivatization, and the polypeptide may be cleaved to obtain fragments that retain activity. Such alterations that do not destroy activity do not remove the polypeptide sequence from the definition of polypeptide of interest as used herein.

The art provides substantial guidance regarding the preparation and use of polypeptide variants. In preparing the polypeptide variants, one of skill in the art can readily determine which modifications to the native protein nucleotide or amino acid sequence will result in a variant that is suitable for use as a therapeutically active component of a pharmaceutical composition of the present invention and whose aggregate formation is decreased by the presence of an amino acid base and an acid substantially free of its salt form, the salt form of the acid, or a mixture of the acid and its salt form, as described herein.

In one embodiment of the invention, the polypeptide present as a therapeutically active component in the liquid pharmaceutical composition of the invention is interleukin-2 (IL-2) or variant thereof, preferably recombinant IL-2. Interleukin-2 is a lymphokine that is produced by normal peripheral blood lymphocytes and is present in the body at low concentrations. It induces the proliferation of antigen- or mitogen-stimulated T cells after exposure to plant lectins, antigens, or other stimuli. IL-2 was first described by Morgan et al. (1976) *Science* 193:1007–1008 and originally called T-cell growth factor because of its ability to induce proliferation of stimulated T lymphocytes. It is a protein with a reported molecular weight in the range of 13,000 to 17,000 (Gillis and Watson (1980) *J. Exp. Med.* 159:1709) and has an isoelectric point in the range of 6–8.5. It is now recognized that in addition to its growth factor properties, it modulates various in vitro and in vivo functions of the immune system. IL-2 is one of several lymphocyte-produced messenger-regulatory molecules that mediate cellular interactions and functions. This naturally occurring lymphokine has been shown to have antitumor eggs 25 activity against a variety of malignancies either alone or when combined with is lymphokine-activated killer (LAK) cells or tumor-infiltrating lymphocytes (see, for example, Rosenberg et al. (1987) *N. Engl. J. Med.* 316:889–897; Rosenberg (1988) *Ann. Surg.* 208:121–135; Topalian et al. 1988) *J. Clin. Oncol.* 6:839–853; Rosenberg et al. (1988) *N. Engl. J. Med.* 319:1676–1680; and Weber et al. (1992) *J. Clin. Oncol.* 10:33–40). Although the anti-tumor activity of IL-2 has best been described in patients with metastatic melanoma and renal cell carcinoma, other diseases, notably lymphoma, also appear to respond to treatment with IL-2.

By "recombinant IL-2" is intended interleukin-2 having comparable biological activity to native-sequence IL-2 and which has been prepared by recombinant DNA techniques as described, for example, by Taniguchi et al. (1983) *Nature* 302:305–310 and Devos (1983) *Nucleic Acids Research* 11:4307–4323 or mutationally altered IL-2 as described by Wang et al. (1984) *Science* 224:1431–1433. In general, the gene coding for IL-2 is cloned and then expressed in transformed organisms, preferably a microorganism, and most preferably *E. coli*, as described herein. The host organism expresses the foreign gene to produce IL-2 under expression conditions. Synthetic recombinant IL-2 can also be made in eukaryotes, such as yeast or human cells. Processes for growing, harvesting, disrupting, or extracting the IL-2 from cells are substantially described in, for example, U.S. Pat. Nos. 4,604,377; 4,738,927; 4,656,132; 4,569,790; 4,748,234; 4,530,787; 4,572,298; and 4,931,543; herein incorporated by reference in their entireties.

For examples of variant IL-2 proteins, see European Patent Application No. 136,489; European Patent Application No. 83101035.0 filed Feb. 3, 1983 (published Oct. 19, 1983 under Publication No. 91539); European Patent Application No. 82307036.2, filed Dec. 22, 1982 (published Sep. 14, 1983 under No. 88195); the recombinant IL-2 muteins described in European Patent Application No. 83306221.9, filed Oct. 13, 1983 (published May 30, 1984 under No. 109748), which is the equivalent to Belgian Patent No. 893,016, commonly owned U.S. Pat. No. 4,518,584; the muteins described in U.S. Pat. Nos. 4,752,585 and WO 99/60128; and the IL-2 mutein used in the examples herein and described in U.S. Pat. No. 4,931,543; all of which are herein incorporated by reference. Additionally, IL-2 can be modified with polyethylene glycol to provide enhanced solubility and an altered pharmokinetic profile (see U.S. Pat. No. 4,766,106, hereby incorporated by reference in its entirety).

In another embodiment of the invention, the polypeptide present as a therapeutically active component in the liquid pharmaceutical composition of the invention is an interferon, more particularly the fibroepithelial β-interferon (IFN-β) or variant thereof, preferably recombinant IFN-β prepared by recombinant DNA techniques described in the art. Interferons are produced by mammalian cells in response to exposure to a variety of inducers, such as mitogens, polypeptides, viruses, and the like. These relatively small, species-specific, single chain polypeptides exhibit immunoregulatory, antiviral, and antiproliferative properties. Interferons are of interest as therapeutic agents for treatment of antiviral diseases and control of cancer.

DNA sequences encoding the human IFN-β gene are available in the art (see Goeddel et al (1980) *Nucleic Acids Res.* 8:4057 and Taniguchi et al (1979) *Proc. Japan acad. Sci.* 855:464) and the gene has been expressed in *E. coli* (Taniguchi et al. (1980) *Gene* 10:11–15) and Chinese hamster ovary cells (see, for example, U.S. Pat. Nos. 4,966,843 and 5,376,567). Variants of IFN-β are described in European Patent Application No. 185459B1, and U.S. Pat. Nos. 4,518,584, 4,588,585, and 4,737,462 describe muteins such as IFN-$\beta_{ser17}$ expressed in *E. coli,* all of which are herein incorporated by reference.

In yet another embodiment, the polypeptide present as a therapeutically active component in the liquid pharmaceutical composition of the invention is tissue factor pathway inhibitor (TFPI) or variant thereof, preferably recombinant TFPI. This polypeptide, which is an inhibitor of the coagulation cascade, is also known as lipoprotein associated coagulation inhibitor (LACI), tissue factor inhibitor (TFI), and extrinsic pathway inhibitor (EPI). TFPI was first purified from a human hepatoma cell, Hep G2 (Broze and Miletich (1987) *Proc. Natl. Acad. Sci. USA* 84:1886–1890) and subsequently from human plasma (Novotny et al. (1989) *J. Biol. Chem.* 264:18832–18837); and Chang liver and SK hepatoma cells (Wun et al. (1990) *J. Biol. Chem.* 265:16096–16101). TFPI cDNA have been isolated from placental and endothelial cDNA libraries (Wun et al. (1988) *J. Biol. Chem.* 263:6001–6004); Girard et al. (1989) *Thromb. Res.* 55:37–50). For reviews, see Rapaport (1989) *Blood* 73:359–365 (1989); Broze et al. (1990) *Biochemistry* 29:7539–7546. The cloning of the TFPI cDNA, which encodes the 276 amino acid residue protein of TFPI, is further described in U.S. Pat. No. 4,966,852; see also U.S. Pat. Nos. 5,773,251 and 5,849,875; all of which are herein incorporated by reference.

Variants of TFPI are known in the art. See, for example, U.S. Pat. No. 5,212,091, where a non-glycosylated form of recombinant TFPI has been produced and isolated from *E coli;* U.S. Pat. No. 5,106,833, where analogues and fragments are disclosed; and U.S. Pat. No. 5,378,614, where production of TFPI analogues in yeast is described; all of which are herein incorporated by reference.

A pharmaceutically effective amount of a stabilized polypeptide-containing liquid pharmaceutical composition of the invention is administered to a subject. By "pharmaceutically effective amount" is intended an amount that is useful in the treatment, prevention or diagnosis of a disease or condition. Typical routes of administration include, but are not limited to, oral administration and parenteral administration, including intravenous, intramuscular, subcutaneous, intraarterial and intraperitoneal injection or infusion. In one such embodiment, the administration is by injection, preferably subcutaneous injection. Injectable forms of the compositions of the invention include, but are not limited to, solutions, suspensions and emulsions.

The stabilized liquid pharmaceutical composition comprising the polypeptide of interest should be formulated in a unit dosage and may be in an injectable or infusible form such as solution, suspension, or emulsion. Furthermore, it can be stored frozen or prepared in the dried form, such as a lyophilized powder, which can be reconstituted into the liquid solution, suspension, or emulsion before administration by any of various methods including oral or parenteral routes of administration. Preferably it is stored in the liquid formulation to take advantage of the increased storage stability achieved in accordance with the methods of the present invention as outlined below. The stabilized pharmaceutical composition is preferably sterilized by membrane filtration and is stored in unit-dose or multi-dose containers such as sealed vials or ampules. Additional methods for formulating a pharmaceutical composition generally known in the art may be used to further enhance storage stability of the liquid pharmaceutical compositions disclosed herein provided they do not adversely affect the beneficial effects of the preferred stabilizing and buffering agents disclosed in the methods of the invention. A thorough if discussion of formulation and selection of pharmaceutically acceptable carriers, stabilizers, etc. can be found in *Remington's Pharmaceutical Sciences* (1990) (18$^{th}$ ed., Mack Pub. Co., Eaton, Pa.), herein incorporated by reference.

By "subject" is intended any animal. Preferably the subject is mammalian, must preferably the subject is human. Mammals of particular importance other than human include, but are not limited to, dogs, cats, cows, horses, sheep, and pigs.

When administration is for the purpose of treatment, administration may be for either a prophylactic or therapeutic purpose. When provided prophylactically, the substance is provided in advance of any symptom. The prophylactic administration of the substance serves to prevent or attenuate any subsequent symptom. When provided therapeutically, the substance is provided at (or shortly after) the onset of a symptom. The therapeutic administration of the substance serves to attenuate any actual symptom.

Thus, for example, formulations comprising an effective amount of a pharmaceutical composition of the invention comprising native-sequence IL-2 or variant thereof can be used for the purpose of treatment, prevention, and diagnosis of a number of clinical indications responsive to therapy with this polypeptide. Biologically active variants of native-sequence IL-2, such as muteins of IL-2 that retain IL-2 activity, in particular the mutein IL-2.sub.ser125 and other muteins in which the cysteine at position 125 has been replaced with another amino acid, can be formulated and used in the same manner as native-sequence IL-2. Accordingly, formulations of the invention comprising native-sequence IL-2 or variant thereof are useful for the diagnosis, prevention, and treatment (local or systemic) of bacterial, viral, parasitic, protozoan and fungal infections; for augmenting cell-mediated cytotoxicity; for stimulating lymphokine activated killer (LAK) cell activity; for mediating recovery of immune function of lymphocytes; for augmenting alloantigen responsiveness; for facilitating recovery of immune function in acquired immune deficient states; for reconstitution of normal immunofunction in aged humans and animals; in the development of diagnostic assays such as those employing enzyme amplification, radiolabelling, radioimaging, and other methods known in the art for monitoring IL-2 levels in the diseased state; for the promotion of T-cell growth in vitro for therapeutic and diagnostic purposes; for blocking receptor sites for lymphokines; and in various other therapeutic, diagnostic and research applications. The various therapeutic and diagnostic applications of human IL-2 or variants thereof, such as IL-2 muteins, have been investigated and reported in Rosenberg et al. (1987) *N. Engl. J. Med.* 316:889–897; Rosenberg (1988) *Ann. Surg.* 208:121–135; Topalian et al. 1988) *J. Clin. Oncol.* 6:839–853; Rosenberg et al. (1988) *N. Engl. J. Med.* 319:1676–1680; Weber et al. (1992) *J. Clin. Oncol.* 10:33–40; Grimm et al. (1982) *Cell. Immunol.* 70(2): 248–259; Mazumder (1997) *Cancer J. Sci. Am.* 3(Suppl. 1):S37–42; Mazumder and Rosenberg (1984) *J. Exp. Med.* 159(2):495–507; and Mazumder et al. (1983) *Cancer Immunol. Immunother.* 15(1):1–10. Formulations of the invention comprising IL-2 or variant thereof may be used as the single therapeutically active agent or may be used in combination with other immunologically relevant B or T cells or other therapeutic agents. Examples of relevant cells are B or T cells, natural killer cells, LAK cells, and the like, and exemplary therapeutic reagents that may be used in combination with IL-2 or variant thereof are the various interferons, especially gamma interferon, B-cell growth factor, IL-1, and antibodies, for example anti-HER2 or anti-CD20 antibodies. Formulations of the invention comprising IL-2 or variant thereof may be administered to humans or animals orally, intraperitoneally, intramuscularly, subcutaneously, intravenously, intranasally, or by pulmonary delivery as deemed appropriate by the physician. The amount of IL-2 (either native-sequence or variant thereof retaining IL-2 biological activity, such as muteins disclosed herein) administered may range between about 0.1 to about 15 mIU/m$^2$. For indications such as renal cell carcinoma and metastatic melanoma, the IL-2 or biologically active variant thereof may be administered as a high-dose intravenous bolus at 300,000 to 800,000 IU/kg/8 hours.

Formulations comprising an effective amount of the pharmaceutical compositions of the invention comprising native-sequence tissue factor pathway inhibitor (TFPI) or variant thereof are useful for the diagnosis, prevention, and treatment (local or systemic) of clinical indications responsive to therapy with this polypeptide. Such clinical indications include, for example, indications associated with increased synthesis and release of neutrophil elastase, such as inflammatory diseases including severe acute pancreatitis, emphysema, rheumatoid arthritis, multiple organ failure, cystic fibrosis, Adult Respiratory Distress Syndrome (ARDS), and sepsis; and for the diagnosis and treatment of diseases associated with increased synthesis and release of IL-8, including inflammatory diseases such as ARDS, reperfasion injury (including lung reperfusion injury), sepsis, and arthritis. See WO 96/40224, herein incorporated by reference. Administration of IFN-β or its muteins to humans or animals may be delivered orally, intraperitoneally, intramuscularly, subcutaneously, intravenously, intranasally, or by pulmonary delivery as deemed appropriate by the physician.

Formulations comprising an effective amount of the pharmaceutical compositions of the invention comprising β-interferon (IFN-β) or variant thereof, such as IFN-β$_{ser17}$, are useful in the diagnosis, prevention, and treatment (local or systemic) of clinical indications responsive to therapy with this polypeptide. Such clinical indications include, for example, disorders or diseases of the central nervous system (CNS), brain, and/or spinal cord, including Alzheimer's disease, Parkinson's disease, Lewy body dementia, multiple sclerosis, epilepsy, cerebellar ataxia, progressive supranuclear palsy, amyotrophic lateral sclerosis, affective disorders, anxiety disorders, obsessive compulsive disorders, personality disorders, attention deficit disorder, attention deficit hyperactivity disorder, Tourette Syndrome, Tay Sachs, Nieman Pick, and schizophrenia; nerve damage from cerebrovascular disorders such as stroke in the brain or spinal cord, from CNS infections including meningitis and HIV, from tumors of the brain and spinal cord, or from a prion disease; autoimmune diseases, including acquired immune deficiency, rheumatoid arthritis, psoriasis, Crohn's disease, Sjogren's syndrome, amyotropic lateral sclerosis, and lupus; and cancers, including breast, prostate, bladder, kidney and colon cancers. Administration of IFN-β or its muteins to humans or animals may be delivered orally, intraperitoneally, intramuscularly, subcutaneously, intravenously, intranasally, or by pulmonary delivery as deemed appropriate by the physician.

The present invention also provides a method for increasing stability of a polypeptide in a liquid pharmaceutical composition, where the polypeptide, which serves as a therapeutically active component, exhibits aggregate formation during storage in a liquid formulation. The method comprises incorporating into the liquid pharmaceutical composition an amino acid base in an amount sufficient to decrease aggregate formation of the polypeptide during storage of the liquid pharmaceutical composition, and an acid substantially free of its salt form, an acid in its salt form, or a mixture of an acid and its salt form, where the acid serves as a buffering agent to maintain the pH of the liquid composition within an acceptable range, as previously described herein.

Increasing stability of a polypeptide or variant thereof by incorporating an amino acid base, or an amino acid base base plus one or more additional stabilizing agents described herein, in combination with the buffering agent disclosed herein, i.e., an acid substantially free of its salt form, the salt form of the acid, or a mixture of the acid and its salt form, leads to an increase in stability of the liquid polypeptide-containing pharmaceutical composition during storage. Thus, the invention also provides a method for increasing storage stability of a liquid pharmaceutical composition when that composition comprises a polypeptide that forms aggregates during storage in a liquid formulation. By "increasing storage stability" is intended the pharmaceutical composition exhibits greater retention of the polypeptide or variant thereof in its proper, nonaggregated, biologically active conformation during storage, and thus less of a decline in therapeutic efficacy, than does a liquid pharmaceutical composition prepared in the absence of an amino acid base, or an amino acid base plus one or more of the additional stabilizing agents described herein, in combination with the buffering agent disclosed herein.

Storage stability of a polypeptide-containing pharmaceutical compositions made in accordance with the methods of the invention can be assessed using standard procedures known in the art. Typically, storage stability of such compositions is assessed using storage stability profiles. These profiles are obtained by monitoring changes in the amount of polypeptide present in its nonaggregated, biologically active molecular form and its potency over time in response to the variable of interest, such as pH concentration, stabilizing agent, concentration of stabilizing agent, etc., as demonstrated in the Examples below. These stability profiles can be generated at several temperatures representative of possible storage conditions, such as freezing temperature, refrigerated temperature, room temperature, or elevated temperature, such as at 40–50° C. Storage stability is then compared between profiles by determining, for example, half-life of the nonaggregated, biologically active molecular form of the polypeptide of interest. By "half-life" is intended the time needed for a 50% decrease in the nonaggregated, biologically active molecular form of the polypeptide of interest. Compositions comprising arginine base and an acid substantially free of its salt form prepared in accordance with the methods of the present invention will have a half life that is at least about two-fold to about ten-fold greater, preferably at least about three-fold to at least about 10-fold greater, more preferably at least about four-fold to about ten-fold greater, most preferably at least about five-fold to about ten-fold greater than the half-life of a liquid composition prepared in the absence of an amino acid base base, or an amino acid base plus one or more of the additional stabilizing agents described herein, in combination with an acid substantially free of its salt form, the salt form of the acid, or a mixture of the acid and its salt form. For purposes of the present invention, a pharmaceutical composition having increased storage stability as a result of being prepared in accordance with the present invention is considered a "stabilized" pharmaceutical composition. Such a stabilized composition preferably has a shelf-life of at least about 18 months, more preferably at least 20 months, still more preferably at least about 22 months, most preferably at least about 24 months when stored at 2–8° C.

The following examples are offered by way of illustration and not by way of limitation.

Experimental

IL-2 is a potent mitogen that stimulates T-cell proliferation. It has wide therapeutic application as a treatment for cancer metastasis, as an adjuvant for cancer therapy, and as a conjunctive agent for infectious diseases.

With the progress of various clinical trials using IL-2 therapy, it has been realized that development of a stable liquid formulation for this protein is highly desirable. Such a formulation would be more versatile than traditional lyophilized formulations, as it could be supplied in different strengths according to various dosing regimens. A liquid formulation would also be more convenient to administer, as no reconstitution would be needed. Such a formulation may be supplied in prefilled, ready-to-use syringes, or as multi-dose preparations if found compatible with bacteriostatic agents.

It has been reported that IL-2 in liquid formulations degrades via at least three pathways during storage: aggregation, methionine oxidation, and deamidation (Kunitani et al. (1986) *J. Chromatography* 359:391–401; Kenney et al. (1986) *Lymphokine Res.* 5:523–527). In addition, IL-2 is susceptible to acute damage caused by freezing and mechanical shearing stress. Therefore, IL-2 formulation development needs to address both acute damage and chronic degradation.

Accordingly, a new stable, monomeric rhIL-2 formulation has been developed. In this formulation, the protein molecules are present in solution in their monomer form, not in an aggregated form. Hence covalent or hydrophobic oligomers or aggregates of rhIL-2 are not present. The formulation contains several stabilizing agents, most importantly arginine and methionine, to stabilize the protein against physical and chemical damages such as aggregation, methionine oxidation, and deamidation during long-term storage. In addition, a nonionic surfactant, polysorbate 80, has been included in the formulation to prohibit the protein from acute damage caused by freeze-thaw and mechanical shearing stress. As shown in the following examples, addition of the stabilizing agents of the invention to the rhIL-2 formulation increases its storage stability.

The IL-2 molecule used in these examples is the recombinant human IL-2 mutein, aldesleukin, with cysteine-125 replaced by serine (des-alanyl-1, serine-125 human interleukin-2). It is expressed from *E. coli*, and subsequently purified by diafiltration and cation exchange chromatography as described in U.S. Pat. No. 4,931,543. Purified bulk for development use was at about 3 mg/ml of IL-2 and was formulated either in 10 mM sodium citrate at pH 6, 200–250 mM NaCl (the CM pool buffer) or in a buffer containing 10 mM sodium succinate at pH 6 and 150 mM L-arginine.

Tissue factor pathway inhibitor (TFPI) is another protein that exhibits degradation by aggregation during storage in a liquid pharmaceutical formulation (Chen et al. (1999) *J. Pharm. Sci.* 88:881–888). Example 8 below is directed to liquid formulations that demonstrate the effectiveness of using an acid in its free base form to decrease aggregate formation and a buffering system supplied by an acid substantially free of its salt form.

The following protocols were used in the examples to determine effect of a particular stabilizing agent on IL-2 or TFPI degradation, and hence stability of this protein during storage in liquid formulations.

UV Absorbance Measurement

UV absorbance of protein solutions was measured using a Hewlett Packard Diode Array spectrometer (Model 8452). The instrument was blanked with the appropriate formulation buffer. Absorbance at 280 nm was recorded using a 1.0 cm pathlength quartz cuvette. The extinction coefficient of 0.70 $(mg/ml)^{-1}$ $cm^{-1}$ was used to convert the absorbance data to IL-2 concentration in mg/ml.

RP-HPLC

RP-HPLC was performed on a Waters 626 LC system equipped with a 717 autosampler (Waters Corporation, Milford, Me.) using a Vydac 214BTP54 $C_4$ column and a Vydac 214GCC54 pre-column (Separations Group, Hesparia, Calif.). The columns were initially equilibrated with a mobile phase A (10% acetonitrile, 0.1% TFA). Then 20 µg of an IL-2 sample was loaded, and the protein was eluted by applying a mobile phase B (100% acetonitrile, 0.1% TFA) from 0 to 100% in 50 minutes at a flow rate of 1.0 ml/min. The main soluble IL-2 species was eluted at approximately 32 min and detected by UV 214 nm using a Waters 486 detector. Data acquisition and processing were performed on a Perkins-Elmer Turbochrom system (PE Nelson, Cupertino, Calif.).

This RP-HPLC method detects the main monomeric IL-2 species as peak B, a methionine oxidative species (mainly oxidized $Met^{104}$) as peak A, a deamidated species (probably $Asn^{88}$) as peak B', and other unknown species eluting either earlier or later than these peaks.

SEC-HPLC

Size exclusion HPLC was performed on a TOSOHAAS G2000SW×1 column and a TSK SW×1 guard column (TOSOHAAS, Montgomeryville, Pa.). A single mobile phase containing 10 mM sodium phosphate at pH 7 and 200 mM ammonium sulfate was applied at a flow rate of 1.0 ml/min. The monomer IL-2 species was eluted at approximately 14 min and detected by UV 214 nm using a Waters 486 detector. Data acquisition and processing were performed on a Perkin-Elmer Turbochrom system.

Using a native SEC-HPLC protocol specially developed to monitor IL-2, the rhIL-2 eluted mainly as a single species, likely in the monomeric form since addition of aggregation dissociation agents, such as SDS, urea, and DTT, did not affect the elution of this species.

IEX-HPLC

Ion exchange(IEX)-HPLC was performed on a Pharmacia Mono-S HR 5/5 glass column using a Waters 626 LC system with a 717 heater/cooler autosampler as described in Chen et al. (1999) *J. Pharm. Sci.* 88:881–888. The column was equilibrated with 80% mobile phase A (70:30 v/v, 20 mM sodium acetate:acetonitrile at pH 5.4) and 20% mobile phase B (70:30 v/v, 20 mM sodium acetate and 1 M ammonium chloride:acetonitrile at pH 5.4). After injection, recombinant human (rh) TFPI was eluted by increasing mobile phase B to 85% in 21 minutes at a flow rate of 0.7 ml/minute. The rhTFPI eluted at approximately 16.5 minutes as a single peak and was detected by UV absorbance at 280 nm with a Waters 486 absorbance detector. Data acquisition and processing were performed on a Perkin-Elmer Turbochrom system. Protein concentration was estimated by integrating the peak area and comparing it with a standard curve generated from samples of known concentrations.

SDS-PAGE

SDS-PAGE was performed according to the Laemmli protocol. About 5 µg of IL-2 was loaded into each lane of a pre-cast 18% Norvex Tris-glycine gel and electrophoresis was carried out at 100 Volts. Protein bands were stained by the Coomassie blue dye and were analyzed by a Molecular Dynamics densitometer equipped with the Imagequan T system (Molecular Dynamics, Sunnyvale, Calif.).

HT-2 Cell Proliferation and MTT Stain for IL-2 Bioactivity

The potency of IL-2 was determined by an in vitro bioassay using HT-2 cell proliferation and MTT stain (Gillis et al. (1978) *J. Immunology* 120:2027–2032; Watson (1979) *J. Exp. Med.* 150(6):1510). Briefly, $1 \times 10^4$ of murine HT-2 cells, which were IL-2 dependent for growth, were loaded into a well of tissue culture plate containing standards, controls, or samples. After 22 to 26 hr incubation at 37° C., MTT stain was added into the wells and incubation was continued at 37° C. for 3 to 4 hr. Then 20% SDS was added for destaining overnight at room temperature. Absorbance of the wells was read at 570 nm and converted to the IL-2 bioactivity based on the WHO International standards.

pH and Osmolarity Measurements

The solution pH of the various formulations was measured by a pH meter from Orion (Model 611, Orion Research Incorporated Laboratory Products Group, Boston, Mass.). The pH meter was calibrated by the two-buffer calibration procedure suggested by the manufacturer using a pH 4 standard (Fisher Scientific, Cat. No. SB101-500) and a pH 7 standard (Fisher Scientific, Cat. No. SB107-500).

The solution osmolarity of these formulations was measured by a Vapor Pressure Osmometer from Wescor (Model 5500, Wescor Inc., Logan, Utah). The osmometer was calibrated by two standards supplied by the manufacturer: 290 mmol/kg standard (Wescor, Reorder No. OA-010) and 1,000 mmol/kg standard (Wescor, Reorder No. OA-029).

These protocols were used to quantify the effects of various stabilizing agents on rhIL-2 degradation via protein aggregation, methionine oxidation, and deamidation.

EXAMPLE 1

Effects of Various Solubilizing Agents on Protein Aggregation and Storage Stability of rhIL-2

Protein aggregation is the major degradation pathway for rhIL-2 in liquid media ranging from mildly acidic to alkaline pH conditions. rhIL-2 in solutions formulated with these pH conditions, when stored at elevated temperatures, quickly results in protein aggregation, which leads to visible precipitation. The visible precipitated protein is removable by filtration through a 0.2 μm filter. The remaining soluble protein in solution can be quantified by a number of analytical assays such as RP-HPLC, SEC-HPLC, and UV absorbance. Aggregation also results in a decrease in bioactivity, which can be determined by the in vitro bioassay described herein.

Using the analytical procedures described herein, the storage stability of rhIL-2 under several conditions was followed by monitoring changes in the amount of soluble rhIL-2 as a function of incubation time at elevated temperatures.

1.A. Effects of Sugars and Amino Acids

The effect of sugars on rhIL-2 storage stability was examined for sorbitol, sucrose, and mannitol in formulations containing 0.2 mg/ml rhIL-2, 10 mM sodium succinate at pH 6, and 270 mM of one of these sugars. The amount of soluble rhIL-2 remaining in stability samples was plotted against incubation time as shown in FIG. 1. The curves of sucrose and mannitol superimposed on each other indicate their effects on IL-2 storage stability are similar. The curve for sorbitol is slightly higher than the other two sugars, suggesting sorbitol has a slightly greater stabilization effect than the other two sugars.

Figure 2:
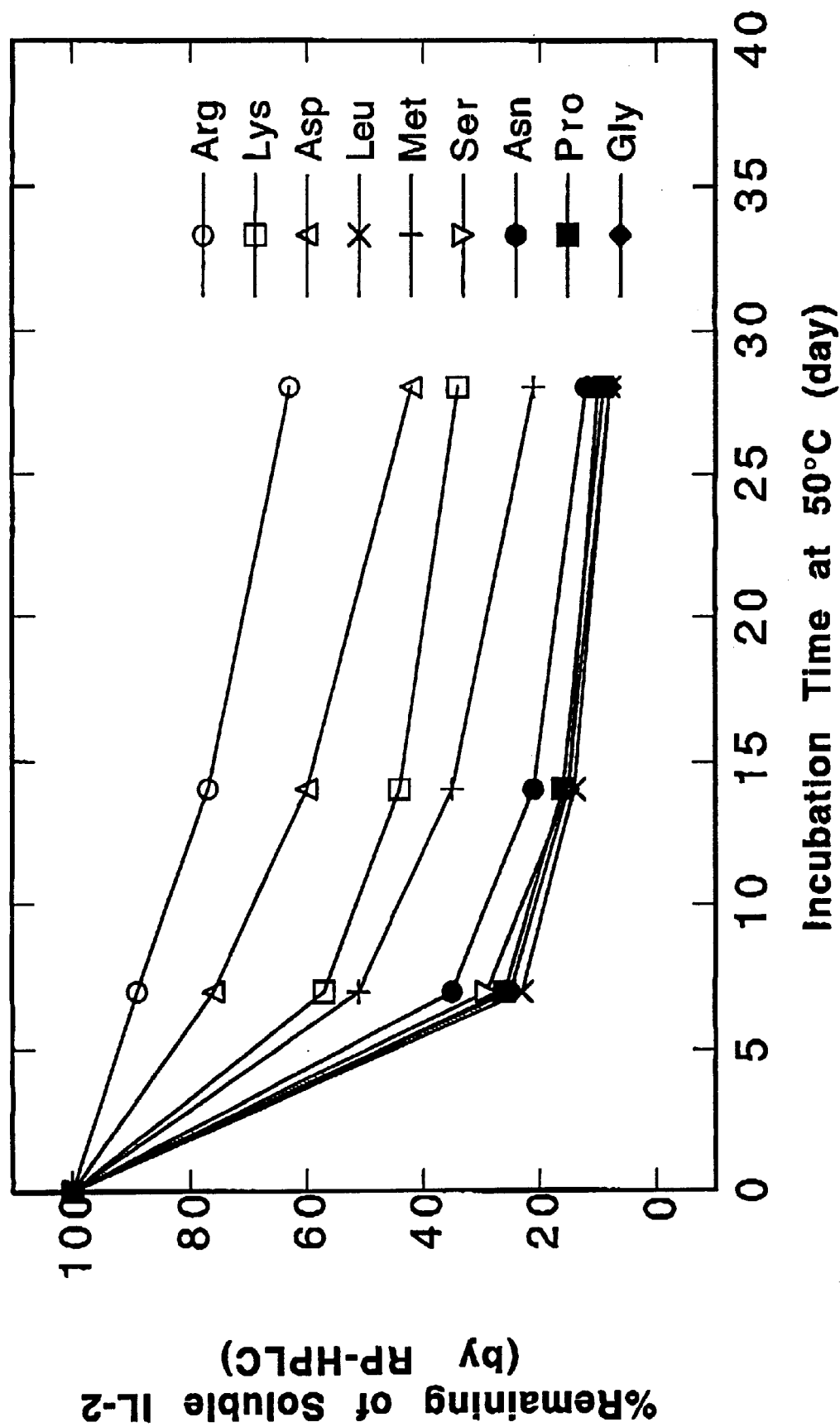
FIG. 2 shows the percent remaining of soluble IL-2 in stability samples stored at 50° C., as analyzed by RP-HPLC. Formulations contained 0.1 mg/ml IL-2, 10 mM sodium succinate at pH 6, and 150 mM of various amino acids as indicated in the figure.

The effect of amino acids on storage stability is shown in FIG. 2. Formulations contained 0.1 mg/ml IL-2, 10 mM sodium succinate at pH 6, and 150 mM of one of the nine amino acids chosen. As shown in FIG. 2, the stability rank is Arg>Asp>Lys>Met>Asn>Leu=Ser=Pro=Gly.

Figure 3:
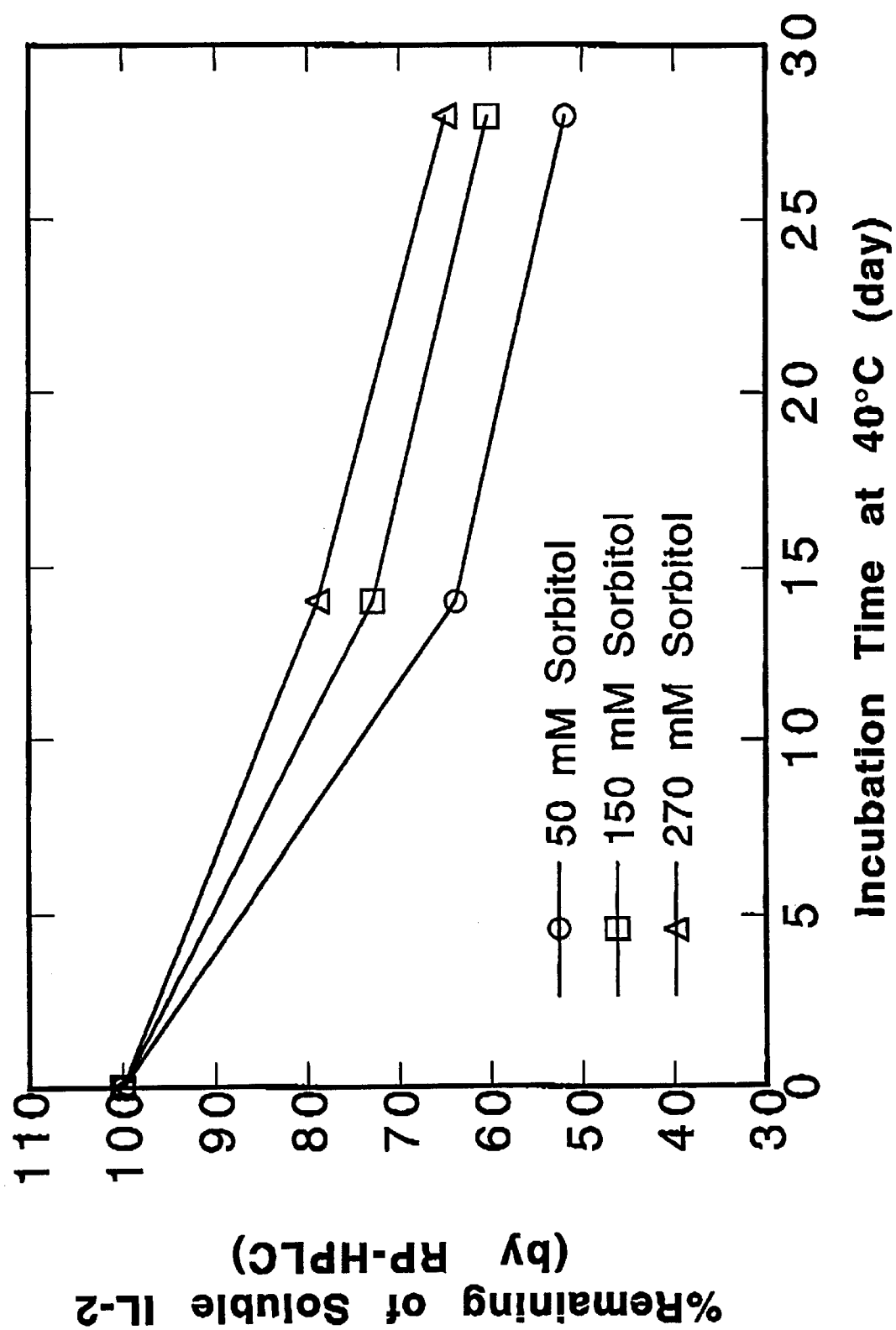
FIG. 3 shows the percent remaining of soluble IL-2 in stability samples stored at 40° C., as analyzed by RP-HPLC. Formulations contained 0.2 mg/ml IL-2, 10 mM sodium succinate at pH 6, and 50, 100, or 270 mM sorbitol.
Figure 4:
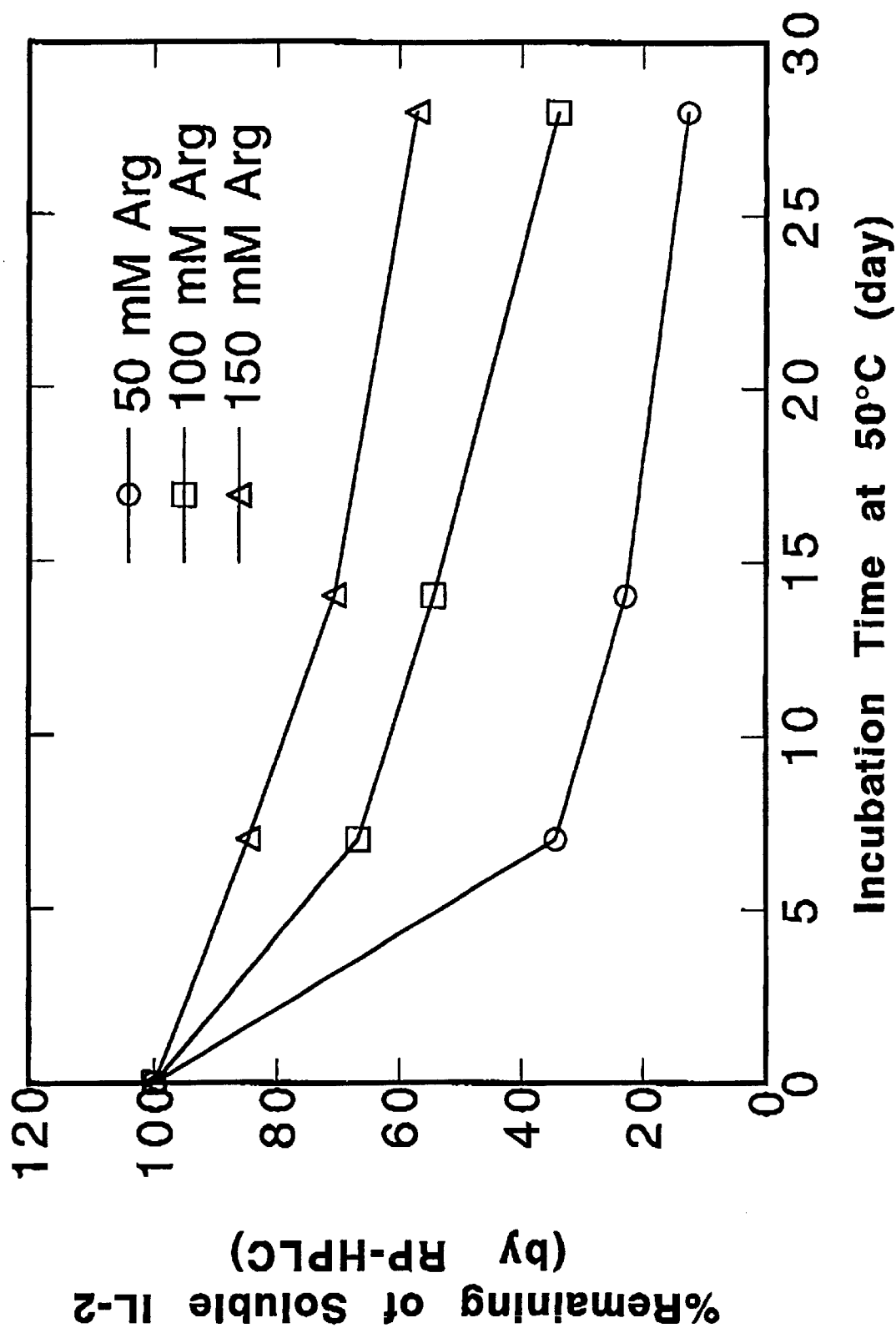
FIG. 4 shows the percent remaining of soluble IL-2 in stability samples stored at 50° C., as analyzed by RP-HPLC. Formulations contained 0.2 mg/ml IL-2, 10 mM sodium succinate at pH 6, and 50, 100, or 150 mM arginine.

The stabilizing effect of sorbitol and arginine was confirmed in further studies, which showed that rhIL-2 storage stability was affected in a concentration dependent manner. Thus, rhIL-2 storage stability is enhanced when sorbitol concentration is increased from 50 mM to 150 mM, and finally to 270 mM (FIG. 3). Similarly, rhIL-2 storage stability increases with increasing concentration of arginine in the formulation (FIG. 4).

1.B. Effect of Formulation pH

The pH storage stability profiles of rhIL-2 in formulations containing NaCl, sorbitol, and arginine were examined. Half-lives for the remaining soluble IL-2 at 50° C. are plotted against pH in FIG. 5. Half-life ($t_{1/2}$) was defined here as the time needed for a 50% decrease in soluble protein in stability samples. Greater half-life indicates greater storage stability.

Figure 5:
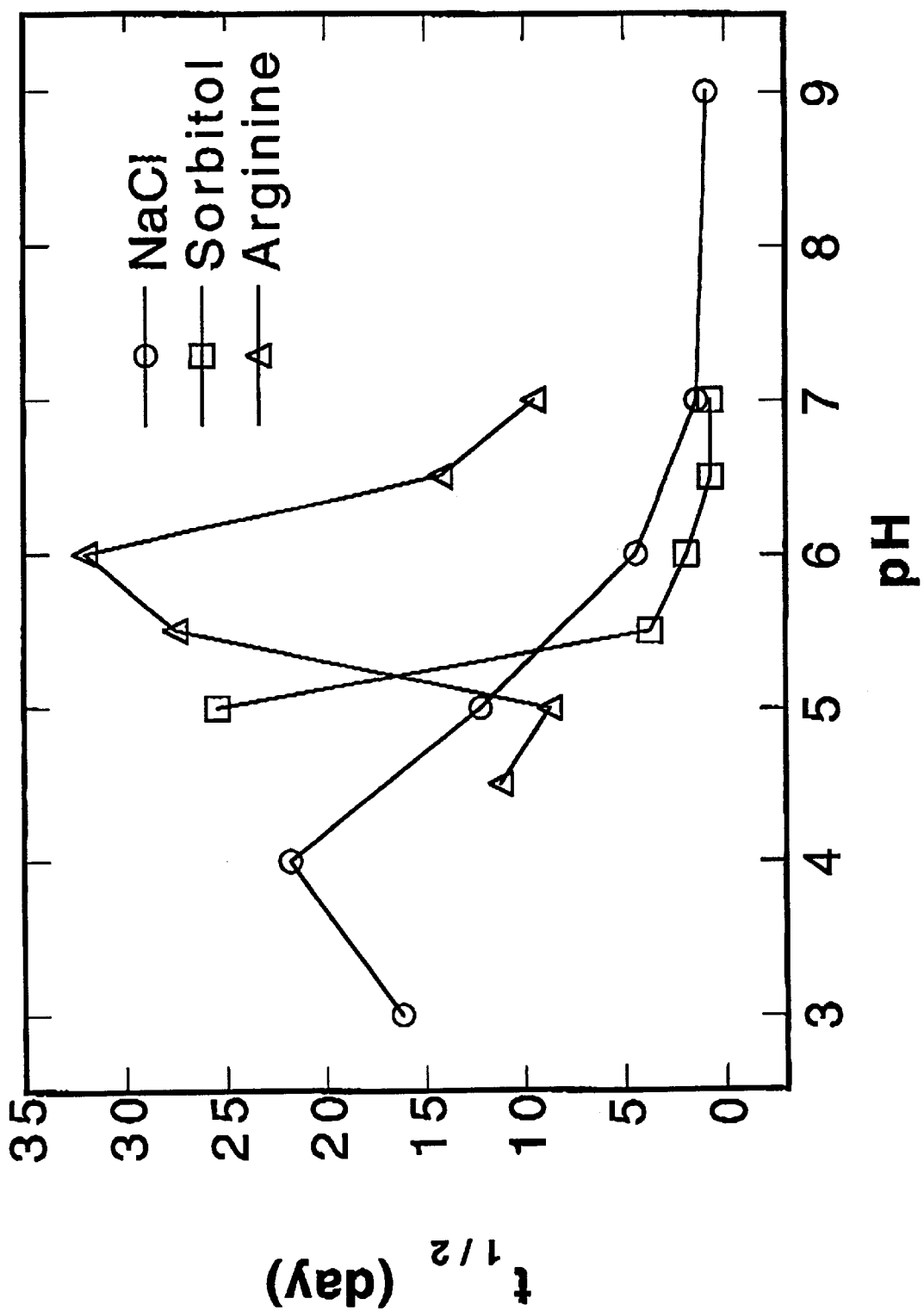
FIG. 5 shows the half-life ($t_{1/2}$, in days) of remaining soluble IL-2 analyzed by RP-HPLC as a function of pH at 50° C. Formulations contained 0.2 mg/ml IL-2, 10 mM buffer (glycine, sodium acetate, sodium citrate, sodium succinate, sodium phosphate, sodium borate), and 150 mM NaCl, 270 mM sorbitol, or 150 mM arginine.

As shown in FIG. 5, pH optimum for stabilizing rhIL-2 against protein aggregation depends upon the stabilizing agent present in solution. Maximum storage stability of rhIL-2 in NaCl is reached at pH 4, where rhIL-2 has a half-life at 50° C. of approximately 23 days. rhIL-2 in sorbitol formulations shows increased stability as pH decreases, with the maximum stability occurring at pH 5, where the half-life at 50° C. is about 26 days. The greatest stability (i.e., longest half-life) could be achieved with arginine as the stabilizing agent, in a formulation having a pH of about 6.0, where the protein's half-life at 50° C. was about 32 days. These results suggest arginine is a preferred stabilizing agent relative to sorbitol or NaCl, as optimum pH for protein stabilization occurs at a more physiologically acceptable pH.

1.C. Effect of Buffer System

It is quite customary to use a 10 mM buffer system in a formulation to provide a proper pH and to maintain a certain amount of buffering capacity. For instance, a formulation pH of 5.8 can be achieved by using 10 mM of a mixture of succinic acid and its salt form, such as sodium succinate. If such a buffer system is selected, 150 mM arginine HCl, but not 150 mM arginine base, can be used as the primary stabilizing agent in the formulation, since 150 mM arginine base would prohibit pH being adjusted down to 5.8 by the 10 mM buffer.

However, arginine HCl gives rise to a higher osmolarity than does arginine base. Thus, a formulation containing 150 mM arginine HCl adjusted to pH 5.8 with 10 mM succinic acid and sodium succinate buffer is already close to isotonicity, having an osmolarity of about 253 mmol/kg, and a half-life at 50° C. of about 8 days (Table 1). Yet a higher concentration of arginine in the formulation is desirable, as storage stability increases with increases in this stabilizing agent. When the concentration of arginine is increased to 230 mM with addition of arginine HCl and pH is adjusted to 5.8 with 10 mM succinic acid and sodium succinate buffer, the half-life at 50° C. is doubled (about 17 days), yet the solution is hypertonic, having an osmolarity of about 372 mmol/kg.

When succinic acid served as the buffering system to adjust solution pH to 5.8 and arginine was present as arginine base, increasing concentration of arginine base to 230 mM resulted in a similar doubling of the half-life at 50° C., increasing it to about 16 days. However, this increase in storage stability was achieved while keeping the solution nearly isotonic, with the formulation having an osmolarity of about 271 mmol/kg (see Table 1). In this manner, 230 mM arginine base could be used in the formulation to increase storage stability of rhIL-2 without exceeding isotonicity of the formulation.

TABLE 1

Solution osmolarity and storage stability of rhIL-2 formulations.
The storage stability is displayed in half-lives ($t_{1/2}$) for remaining soluble rhIL-2 measured by RP-HPLC after storage at 50° C. Arginine HCl formulations contained 0.5 mg/ml rhIL-2, 1 mM EDTA, and 150 mM or 230 mM L-arginine HCl and 10 mM of succinic acid and sodium succinate to adjust pH to 5.8. Arginine base formulations contained 0.5 mg/ml rhIL-2, 1 mM EDTA, and 150 mM or 230 mM L-arginine base and 81 mM or 128 mM succinic acid to adjust pH to 5.8.

| Formulation (all contained 1 mM EDTA and at pH 5.8) | Osmolarity (mmol/kg) | $t_{1/2}$ at 50° C. (day) |
|---|---|---|
| 150 mM ArgHCl, 10 mM Na Succinate/Succinic acid | 253 | 8.0 |
| 150 mM ArgBase, 81 mM Succinic acid | 192 | 9.9 |
| 230 mM ArgHCl 10 mM Na Succinate/Succinic acid | 372 | 16.9 |
| 230 mM ArgBase, 128 mM Succinic acid | 271 | 16.0 |

These two pH adjustment methods were examined with other buffer systems (Table 2). When 150 mM arginine HCl was used in the formulation and pH was adjusted to 5.8 by 10 mM of an acid and its sodium salt, all formulations were below isotonic, which is approximately 290 mmol/kg. The half-life at 50° C. for the rhIL-2 in these formulations ranged from about 15 to about 20 days. When 230 mM arginine base was used in the formulation and pH was titrated to 5.8 using an acid substantially free its salt form as the buffer system, formulations having pH adjusted with citric acid or succinic acid showed solution osmolarities still below isotonic, while other formulations were either slightly above isotonic, as in the case of phosphoric acid, or hypertonic, as in the case of glutamic or acetic acid. However, the half-life at 50° C. for all formulations was increased to above 30 days. Thus, by using citric acid or succinic acid, both substantially free of their salt forms, as the buffering system, the concentration of arginine could be increased to 230 mM using arginine base, resulting in increased storage stability of rhIL-2.

TABLE 2

Solution osmolarity and storage stability of rhIL-2 formulations.
The storage stability is displayed in half-lives ($t_{1/2}$) for remaining soluble rhIL-2 measured by RP-HPLC after storage at 50° C. All formulations contained 0.2 mg/ml rhIL-2, 5 mM methionine, 1 mM disodium EDTA, 0.1% polysorbate 80 and 150 mM L-arginine HCl with pH adjusted to 5.8 by 10 mM of an acid and its sodium salt or 230 mM L-arginine base with pH adjusted to 5.8 by titrating with an acid substantially free of its salt form.

| Formulation | Osmolarity (mmol/kg) | $t_{1/2}$ (day) |
|---|---|---|
| 150 mM ArgHCl, 10 mM Sodium Citrate/Citric Acid | 248 | 20.5 |
| 230 mM ArgBase, 86 mM Citric Acid | 228 | 36.1 |
| 150 mM ArgHCl, 10 mM Sodium Succinate/Succinic Acid | 257 | 19.1 |
| 230 mM ArgBase, 128 mM Succinic Acid | 285 | 29.2 |
| 150 mM ArgHCl, 10 mM Sodium Phosphate/Phosphoric Acid | 260 | 15.6 |
| 230 mM ArgBase, 193 mM Phosphoric Acid | 329 | 29.9 |
| 150 mM ArgHCl, 10 mM Sodium Glutamate/Glutamic Acid | 264 | 14.6 |
| 230 mM ArgBase, 225 mM Glutamic Acid | 407 | 47.5 |

TABLE 2-continued

Solution osmolarity and storage stability of rhIL-2 formulations.
The storage stability is displayed in half-lives ($t_{1/2}$) for remaining soluble rhIL-2 measured by RP-HPLC after storage at 50° C. All formulations contained 0.2 mg/ml rhIL-2, 5 mM methionine, 1 mM disodium EDTA, 0.1% polysorbate 80 and 150 mM L-arginine HCl with pH adjusted to 5.8 by 10 mM of an acid and its sodium salt or 230 mM L-arginine base with pH adjusted to 5.8 by titrating with an acid substantially free of its salt form.

| Formulation | Osmolarity (mmol/kg) | $t_{1/2}$ (day) |
|---|---|---|
| 150 mM ArgHCl, 10 mM Sodium Acetate/Acetic Acid | 259 | 20.8 |
| 230 mM ArgBase, 250 mM Acetic Acid | 408 | 31.9 |

1.D. Effect of Protein Concentration

Figure 6:
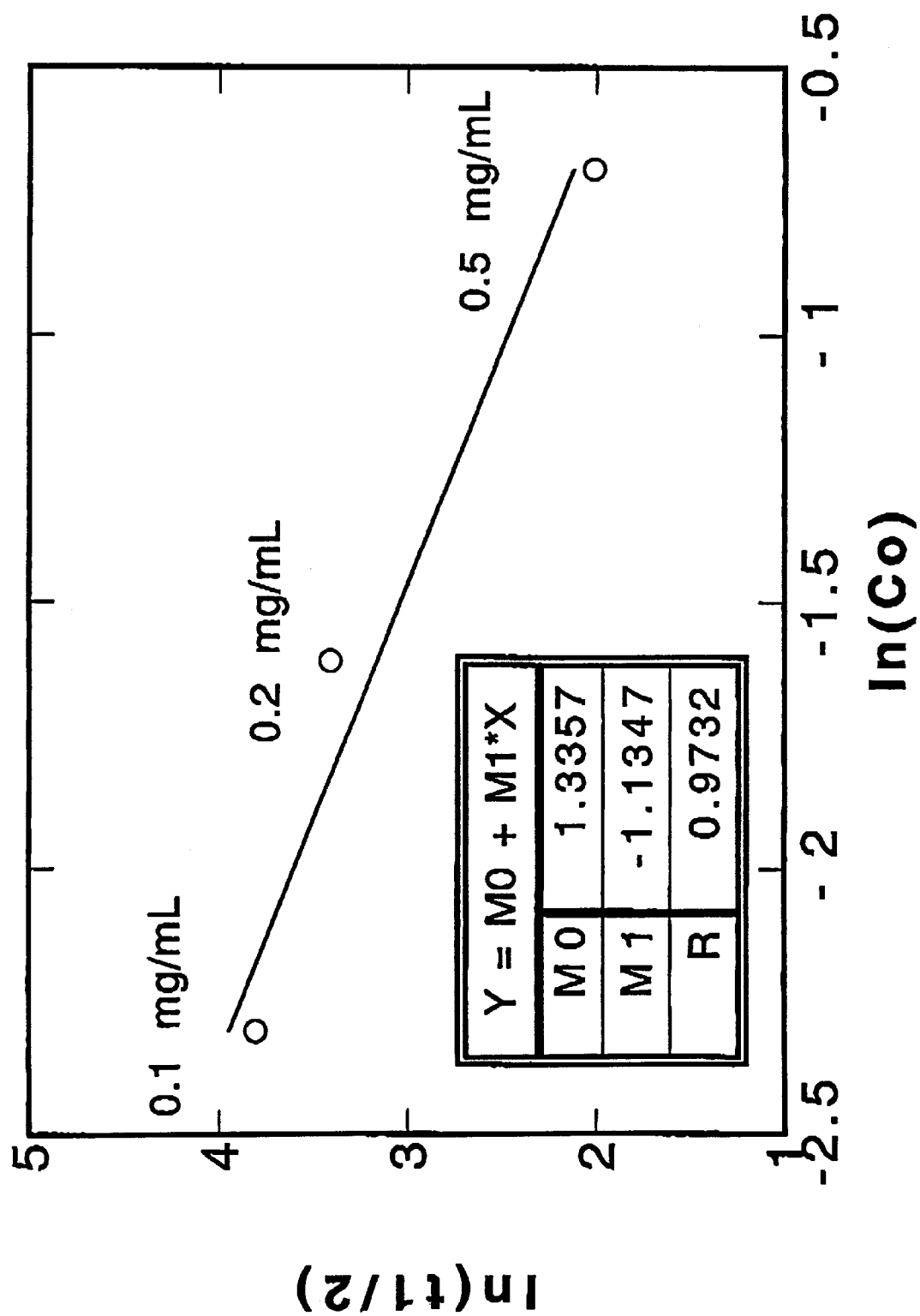
FIG. 6 shows the Ln—Ln plot of half-life ($t_{1/2}$) versus initial protein concentration for stability samples stored at 50° C. Formulations contained 0.1, 0.2, or 0.5 mg/ml IL-2 in 10 mM sodium succinate at pH 6 and 150 mM L-arginine.

The effect of protein concentration on storage stability was examined in a formulation containing 10 mM sodium succinate at pH 6 and 150 mM arginine. As shown in FIG. 6, in which the half-life at 50° C. for soluble rhIL-2 was plotted against initial protein concentration, rhIL-2 storage stability increases as protein concentration decreases. This finding is in agreement with the experimental observation that aggregation is the major degradation pathway for rhIL-2 in liquid formulations.

1.E. Effect of the Nonionic Surfactant Polysorbate 80

Effect of polysorbate 80 (Tween 80 or Tw 80) on rhIL-2 storage stability was tested in a formulation containing 0.5 mg/ml IL-2, 230 mM arginine base, 128 mM succinic acid to adjust pH to 5.8, 1 mM EDTA and 0, 0.02, and 0.1% polysorbate 80. As shown in Table 3, both formulations containing polysorbate 80 exhibit a reduction in the half-life of soluble IL-2 at 50° C., from 16 days to about 9 days as measured by RP-HPLC. Thus, including polysorbate 80 in the formulation would be perceived as unfavorable based solely on its effect on protein aggregation. However, this agent has a stabilizing effect against acute protein damage associated with freeze-thaw and mechanical shearing that is beneficial during processing of liquid formulations containing this protein, as disclosed in the examples below.

Storage stability of two sorbitol-based formulations was also examined. Although their half-lives by RP-HPLC and bioactivity were comparable to the arginine formulations, the half-lives estimated from SEC-HPLC were much smaller, suggesting a larger portion of the rhIL-2 protein in these formulations is probably present in soluble aggregated forms.

TABLE 3

Half-lives (t½) or remaining soluble rhIL-2 (peak B) measured by RP-HPLC, SEC-HPLC, and the in vitro bioassay in rhIL-2 formulations stored at 50° C.

| Formulation | $t_{1/2}$ at 50° C. (day) | | |
|---|---|---|---|
| (all at pH 5.8 and 1 mM EDTA) | RP | SEC | Bioactivity |
| 230 mM ArgBase, 128 mM Suc acid, pH 5.8 | 16.0 | 21.3 | 25.6 |
| 230 mM ArgBase, 128 mM Suc acid, 0.02% Tw 80, pH 5.8 | 9.7 | 12.4 | NA |
| 230 mM ArgBase, 128 mM Suc acid, 0.1% Tw 80, pH 5.8 | 9.1 | 12.2 | 24.5 |
| 270 mM sorbitol, 10 mM NaSuc, 0.1%, Tw 80, pH 4.5 | 31.7 | 3.6 | NA |
| 270 mM sorbitol, 10 mM NaSuc, 0.1% Tw 80, pH 5.0 | 14.4 | 2.4 | 21.3 |

In Table 3, the half-life for an arginine base-succinic acid rhIL-2 formulation as determined by the RP-HPLC method is slightly smaller than that determined by the SEC-HPLC method, and is much smaller than that determined by the in vitro bioassay method. The elution of the main rhIL-2 species on SEC-HPLC was evaluated to further examine these differences. Samples with and without treatment of SDS, urea, and DTT showed no change in the elution time for the main species, indicating that the rhIL-2 in these formulations was present as a monomeric species. However, the SEC-HPLC protocol might not be able to distinguish other monomeric species, for example, the peak A methionine oxidative species, from the major monomeric intact species, the peak B species. Therefore, a small difference in determining the half-life would be expected.

The in vitro bioassay used to determine bioactivity in the data presented in Table 3 was carried out with 0.1% SDS in the assay diluent. Thus, prior to applying samples to the tissue culture plate to interact with murine HT-2 cells, the samples were diluted with assay diluent containing 0.1% SDS. It was possible that dilution with SDS might have dissociated some rhIL-2 aggregate in these samples back to the monomeric form, resulting in an overestimate of the bioactivity of a given formulation. Therefore, stability samples were assayed using assay diluent with (+S) and without (–S) the addition of SDS. Samples were also assayed with (+F) and without (–F) a 0.2 μm filtration treatment, since filtration is able to remove large protein aggregates as judged by visual inspection. Bioactivity values measured for samples with these treatments are shown in Table 4 along with storage stability results obtained using the RP-HPLC protocol for comparison. Values are presented as a percentage of the bioactivity values obtained in similar samples stored at –70 ° C.

In general, the formulations diluted with SDS and not filtered prior to contact with HT-2 cells show higher bioactivity values than those formulations diluted without SDS in the assay diluent and filtered prior to running the assay. Among these bioactivity results, those obtained using filtration and diluting with no SDS are quite comparable with RP-HPLC results. Thus, this method is recommended for the true bioactivity measurement for monomeric rhIL-2.

TABLE 4

Comparison of results between RP-HPLC analysis for soluble rhIL-2 and in vitro bioactivity analysis for stability samples stored 2 wk at 40° C. or 50° C.
All results are presented as percentages of those obtained for their respective –70° C. samples. Formulations contained 0.5 mg/ml rhIL-2, 230 mM L-arginine base, 128 mM succinic acid at pH 5.8, and 1 mM EDTA, with (#1) and without (#2) 0.1% polysorbate 80. Samples for the bioassay were treated with and without a 0.22 μm filtration before dilution using diluents with and without 0.1% SDS.

| Sample | % Bioactivity (percentage to –70° C. samples) | | | | % RP (percentage to –70° C. samples) |
|---|---|---|---|---|---|
| HPLC | –F+S[a] | +F+S[a] | –F–S[a] | +F–S[ab] | |
| #1 at 40° C. | 106 | 100 | 104 | 100 | 101 |
| #1 at 50° C. | 92 | 79 | 60 | 53 | 58 |
| #2 at 40° C. | 101 | 69 | 106 | 112 | 98 |
| #2 at 50° C. | 60 | 38 | 62 | 47 | 42 |

[a]"–F" for non-filtered, "+F" for filtered, "–S" for diluent without SDS and "+S" for diluent with SDS.
[b]This is the recommended protocol for monomeric IL-2.

1.F. Preservative Compatibility

Preservative compatibility was investigated in the need to develop a multidose formulation. Effect of preservatives on IL-2 stability was evaluated in two accelerated studies. Study 1 screened benzyl alcohol, m-cresol, and phenol in a formulation containing 0.2 mg/ml IL-2, 10 mM sodium succinate at pH 6 and 160 mM arginine. Study 2 screened benzethonium chloride, benzalkonium chloride, methyl paragen/propyl parben, and chlorobutanol in a formulation containing 0.2 mg/ml Il-2, 230 mM L-arginine base, 128 mM succinic acid at pH 5.8, 1 mM disodium EDTA, 0.1% polysorbate 80. The half-lives for soluble rhIL-2 measured by RP-HPLC for these formulations stored at 40° C. are presented in Table 5.

All tested preservatives decreased rhIL-2 stability at the elevated temperature. In study 1, the half-life for the soluble rhIL-2 was about 74 days at 40° C. without any of the preservatives. Addition of benzyl alcohol or m-cresol or phenol reduced the half-life significantly by 5- to 10-fold. In study 2, the effects of preservatives were much less intense. The half-life for the soluble rhIL-2 decreased less than half for benzethonium chloride and decreased more than 2-fold for other preservatives. Overall, benzethonium chloride has the least reduction in rhIL-2 stability among the preservatives tested.

TABLE 5

Half-life ($t_{1/2}$) of the soluble rhIL-2 at 40° C. for formulations containing preservatives. Study 1: formulations contained 0.2 mg/ml rhIL-2, 10 mM sodium succinate at pH 6, 150 mM L-arginine and preservatives. Study 2: formulations contained 0.2 mg/ml rhIL-2, 230 mM L-arginine base, 128 mM succinic acid at pH 5.8, 1 mM disodium EDTA, 0.1% polysorbate 80, and preservatives.

| Preservative | $t_{1/2}$ at 40° C. (day) |
|---|---|
| Study 1 | |
| No preservative | 74.0 |
| 0.9% (w/v) benzyl alcohol | 16.0 |
| 0.25% (w/v) m-cresol | 7.5 |
| 0.5% (w/v) phenol | 11.0 |
| Study 2 | |
| No preservative | 261.0 |
| 0.01% (w/v) benzethonium chloride | 185.0 |
| 0.01% (w/v) benzalkonium chloride | 67.0 |
| 0.18% (w/v) methyl paraben and 0.02% (w/v) propyl paraben | 113.0 |
| 0.5% (w/v) chlorobutanol | 84.0 |

Although preservatives had a pronounced destabilizing effect on rhIL-2 at the elevated temperature, their effects on rhIL-2 short-term storage stability at 4° C. or 25° C. were also examined. A new study was carried out to examine six preservatives in a same formulation containing 0.2 mg/ml rhIL-2, 230 mM L-arginine base, 128 mM succinic acid, 1 mM EDTA, 5mM methionine, and 0.1% polysorbate 80 at pH 5.8. Table 6 reports results of the amount of soluble rhIL-2 retained after one year of storage. All formulations, when compared to the control, show no significant loss in the soluble rhIL-2 level by both the RP-HPLC and the in vitro bioassay, with the exception of the formulation containing 0.25% m-cresol, which showed detectable loss.

TABLE 6

One year storage stability of preservative-containing formulations at 4° C. or 25° C. presented in percentage of total soluble rhIL-2 remaining as determined by the RP-HPLC integrated peak areas and the in vitro bioactivity. The control formulation contained 0.2 mg/ml IL-2, 230 mM L-arginine base, 128 mM succinic acid, 1 mM EDTA, 5 mM methionine, and 0.1% polysorbate 80 at pH 5.8.

| Preservative | % of Initial IL-2 by RP-HPLC | | In vitro bioactivity ($\times 10^6$ IU/ml) | | |
|---|---|---|---|---|---|
| | 4° C. | 25° C. | t = 0 | 1 yr/4° C. | 25° C./1 yr |
| Control | 102 | 93 | 3.8 | 3.3 | 2.5 |
| 0.9% benzyl alcohol | 100 | 88 | 4.8 | 4.0 | 5.0 |
| 0.25% m-cresol | 98 | 60 | 5.8 | 2.6 | 2.5 |
| 0.5% phenol | 99 | 87 | 4.7 | 3.9 | 3.2 |
| 0.01% benzalkonium chloride | 102 | 93 | 5.5 | 3.9 | 4.4 |
| 0.01% benzethonium chloride | 98 | 89 | 5.4 | 3.2 | 4.7 |
| 0.5% chlorobutanol | 99 | 91 | 5.1 | 3.6 | 4.5 |

EXAMPLE 2

Effects of Various Factors on Methionine Oxidation and Storage Stability of rhIL-2

Methionine oxidation in IL-2 has been characterized previously (Kunitani et al. (1986) *J. Chromatography* 359:391–402; Sasaoki et al. (1989) *Chem. Pharm. Bull.* 37(8):2160–2164). Il-2 has four methionine residues at residue positions 23, 39, 36 and 104 on the polypeptide chain. Among these, $Met^{104}$ is on the protein surface and is most oxidative. This methionine oxidative species can be resolved as an earlier eluting species (peak A) to the main IL-2 species (peak B) from the RP-HPLC chromatogram. $Met^{23}$ and $Met^{39}$ are less prone to oxidation, which only occurs under extreme oxidative conditions, probably due to their existence in the interior of the protein molecule. Oxidative species of these MET residues may elute as earlier species than the $Met^{104}$ on RP-HPLC. $Met^{46}$ is buried deep inside of the protein molecule and is not easily oxidized unless the protein completely unfolds.

Investigation of methionine oxidation in IL-2 concentrated on oxidation of $Met^{104}$, as it is the most susceptible methionine residue to oxidation and prevention of its oxidation will also prohibit oxidation of other methionine residues.

2.A. Effect of pH

Methionine oxidation was studied at a pH range from 3 to 9 in formulations containing 0.2 mg/ml IL-2, 150 mM NaCl, and 10 mM of various buffer species. Methionine oxidation in these formulations was examined by quantifying percentage of the peak A species (i.e., the $Met^{104}$ oxidized species) in IL-2 samples at t=0 and t=3 months. As reported in Table 7, effect of pH is not noticed at t=0 except in the sample buffered by citrate at pH 6. Compared with other samples, which have 5% of the peak A species, the citrate sample showed an increase in the level of peak A to 6%.

At t=3 months, the level of peak A is increased at higher pH conditions, suggesting a base-catalyzed mechanism for methionine oxidation of Met $^{104}$. At pH 6, succinate is a better buffer than citrate in minimizing methionine oxidation, as lower values of peak A are observed in the succinate formulation.

TABLE 7

RP-HPLC analysis of methionine oxidation, expressed as percentage of the total amount of soluble IL-2 (peak A + peak B) present as the methionine-oxidized peak A species (% peak A of total soluble IL-2) for pH 3 to pH 9 formation samples at t = 0 and 3 months. Formulations contained 0.2 mg/ml IL-2, 150 mM NaCl, and pH adjusted by 10 mM of various buffer species.

| | % peak A of total soluble IL-2 | | | | |
|---|---|---|---|---|---|
| | | t = 3 months | | | |
| Buffer and pH | t = 0 | −70° C. | 4° C. | 25° C. | 40° C. |
| 10 mM Glycine, pH 3 | 5 | 4 | 5 | 6 | 7 |
| 10 mM Acetate, pH 4 | 5 | 5 | 6 | 7 | 6 |
| 10 mM Acetate, pH 5 | NA | 7 | 8 | 9 | 9 |
| 10 mM Citrate, pH 6 | 6 | 6 | 8 | 12 | 14 |
| 10 mM Succinate, pH 6 | 5 | 6 | 7 | 4 | 9 |
| 10 mM Phosphate, pH 7 | 5 | 7 | 8 | 11 | 5 |
| 10 mM Borate, pH 9 | 5 | 11 | 15 | 14 | NA |

2.B. Effects of EDTA, Polysorbate 20, Polysorbate 80, and $MgCl_2$

The effects of a metal chelator, two nonionic surfactants, and a divalent metal ion on methionine oxidation are reported in Table 8. The presence of polysorbate 20 or polysorbate 80 in the formulations increases the level of the methionine oxidative species at both t=0 and t=1 month. In contrast, EDTA and $MgCl_2$ reduce the level of methionine oxidative species after 1 month storage at 40 and 50° C.

TABLE 8

Percentage of the total amount of soluble IL-2 (peak A + peak B) present as the methionine-oxidized peak A species (% peak A) in IL-2 samples at t = 0 and t = 1 month. The control sample contained 0.2 mg/ml IL-2, 10 mM sodium succinate at pH 6, and 150 mM arginine.

| | % peak A (methionine oxidation) | | | | |
|---|---|---|---|---|---|
| | | t = 1 month | | | |
| Formulation | t = 0 | −70° C. | 4° C. | 40° C. | 50° C. |
| Control | 2.8 | 3.5 | 5.1 | 19.7 | 36.3 |
| 1 mM EDTA | 2.5 | 3.5 | 5.0 | 9.5 | 14.0 |
| 0.1% polysorbate 80 | 5.8 | 4.3 | 6.9 | 21.5 | 41.4 |
| 1 mM EDTA + 0.1% polysorbate 80 | 5.9 | 4.2 | 6.9 | 12.1 | 19.2 |
| 0.1% polysorbate 20 | 4.1 | 5.4 | 9.6 | 25.3 | 42.8 |
| 5 mM $MgCl_2$ | 3.9 | 4.8 | 6.9 | 9.7 | 12.1 |

2.C. Effect of Methionine

The addition of methionine in formulations to prevent IL-2 from methionine oxidation was investigated. Table 9 reports change in peak A and total amount of soluble IL-2 (peak A+peak B) for formulations containing varying amounts of methionine after 2 weeks of storage at 50° C. Increasing of methionine concentration in the formulations reduces the level of peak A significantly at both t=0 and 2 weeks, while the amount of soluble IL-2 retained after 2 weeks storage is not affected. At 5 mM methionine, a 3-fold decline in peak A is observed at t=2 weeks. Thus, addition of methionine results in a significant reduction in methionine oxidation of the protein and has little effect on IL-2 aggregation.

TABLE 9

Change in peak A and in total soluble protein in Il-2 samples at t = 0 and t = 2 weeks at 50° C. Formulations contained 0.2 mg/ml IL-2, 230 mM arginine, 128 mM succinic acid at pH 5.8, 1 mM EDTA, 0.1% polysorbate 80 and 0 to 10 mM methionine.

| Formulation | % peak A (methionine oxidation) | | % IL-2 remaining |
|---|---|---|---|
| | t = 0 | t = 2 wk at 50° C. | t = 2 wk at 50° C. |
| No Methionine | 2.1 | 6.3 | 76 |
| 1 mM Methionine | 1.4 | 2.7 | 77 |
| 5 mM Methionine | 1.2 | 2.1 | 77 |
| 10 mM Methionine | 1.2 | 1.9 | 76 |

In addition to the high temperature results, level of methionine oxidation at 4° C. and 25° C. after 3 months storage for formulations with and without 5 mM methionine was also recorded. As shown in Table 10, the presence of 5 mM methionine in the formulation results in a 3-fold decrease in the level of peak A both at 4° C. and at 25° C. Thus, addition of 5 mM methionine effectively prevented the $Met^{104}$ from oxidation.

TABLE 10

Level of methionine oxidation, expressed as percentage of the total amount of soluble IL-2 (peak A + peak B) present as the methionine-oxidized peak A species (% peak A of total soluble IL-2) and percentage of soluble IL-2 remaining in samples stored for 3 months at either 4° C. or at 25° C. Formulations contained 0.2 mg/ml IL-2, 230 mM arginine, 128 mM succinic acid at pH 5.8, 1 mM EDTA, 0.1% polysorbate 80, and 0 or 5 mM methionine.

| Formulation | % peak A of total soluble IL-2 | | % IL-2 remaining (main peak) | |
|---|---|---|---|---|
| | 4° C. | 25° C. | 4° C. | 25° C. |
| 0 mM | 2.7 | 4.1 | 101 | 97 |
| 5 mM | 0.8 | 1.4 | 101 | 100 |

2.D. Effect of Oxygen Removal by Nitrogen Purging and Degassing

Removing oxygen in Il-2 sample vials to minimize methionine oxidation was tested. Air in the headspace in a 3-cc vial with 1 ml IL-2 sample fill was purged with nitrogen. Dissolved molecular oxygen was removed by vacuum degassing. Table 11 shows the change in peak A and total amount of soluble IL-2 (peak A+peak B) after 1 week of storage at 50° C. for these samples. Nitrogen purging alone slightly decreases the percentage of the methionine oxidative species from 6.7% to 6.2%. The combination of solution degassing and nitrogen purging of the headspace further reduces the level of peak A by about one percentage point. On the other hand, the percentage of total amount of soluble IL-2 remains unchanged with either nitrogen purge or degassing.

TABLE 11

Change in percentage of the total amount of soluble IL-2 (peak A + peak B) present as the methionine-oxidized peak A species (% peak A) and in percentage of the total amount of soluble IL=2 remaining in samples withdrawn at t = 0 and t = 1 week at 50° C. Formulations contained 0.3 mg/ml of IL-2, 230 mM arginine, 128 mM succinic acid, 1 mM EDTA, and 0.1% polysorbate 80.

| Formulation | % peak A (methionine oxidation) | | % IL-2 remaining |
|---|---|---|---|
| | t = 0 | t = 1 wk at 50° C. | t = 1 wk at 50° C. |
| Control | 3.1 | 6.7 | 81 |
| Nitrogen purging | 3.1 | 6.2 | 82 |
| Degassing/nitrogen purging | 3.0 | 5.8 | 81 |

2.E. Effect of Preservatives

The effect of preservatives on methionine oxidation was examined. Table 12 shows change in peak A for formulation samples with and without one of the six preservatives after 6 and 12 months storage at 4° C. and at 25° C. All formulations containing preservatives showed similar level of peak A to the control indicating the preservatives have no detectable effect on methionine oxidation except in the formulation containing 0.25% m-cresol, which showed a significant increase in the peak A level.

TABLE 12

Percentage of the total amount of soluble IL-2 (peak A + peak B) present as the methionine-oxidized peak A species (% peak A) and in various preservative-containing formulations stored 6 months and 12 months at 4° C. and 25° C. The control formulation contained 0.2 mg/ml of IL-2, 230 mM L-arginine base, 128 mM succinic acid, 1 mM EDTA, 5 mM methionine, 0.1% polysorbate 80, at a pH of 5.8.

| Preservative | % peak A (methionine oxidation) | | | | |
|---|---|---|---|---|---|
| | | 6 months | | 2 months | |
| | t = 0 | 4° C. | 25° C. | 4° C. | 25° C. |
| Control | 1.5 | 1.6 | 1.9 | 1.8 | 2.6 |
| 0.9% benzyl alcohol | 1.6 | 1.7 | 2.3 | 1.9 | 3.3 |
| 0.25% m-cresol | 1.6 | 1.8 | 6.7 | 2.1 | 3.5 |
| 0.5% phenol | 1.6 | 1.7 | 2.4 | 1.8 | 3.6 |
| 0.01 benzalkonium chloride | 1.5 | 1.6 | 2.0 | 1.0 | 3.0 |
| 0.01% benzethonium chloride | 1.5 | 1.7 | 2.0 | 1.8 | 2.8 |
| 0.5% chlorobutanol | 1.5 | 1.6 | 2.0 | 1.8 | 3.2 |

EXAMPLE 3

Effect of Various Factors on Deamidation of IL-2

Deamidation of Il-2 has been reported previously (Kunitani et al. (1986) *J. Chromatography* 359:391–402). $Asp^8$ has been discovered to be the primary site for deamidation in IL-2 (Sasaoki et al. (1992) *Chem. Pharm. Bull.* 40(4):976–980). Deamidated species can be detected by RP-HPLC as a back shoulder peak (Peak B') to the main species (peak B). IL-2 deamidation was studied in formulations containing arginine, NaCl, and sorbitol. Table 13 shows that deamidated species can be detected only in formulations containing sorbitol and NaCl, but not in formulations containing arginine, after incubation at elevated temperatures for 2 weeks. Therefore, arginine stabilizes IL-2 against degradation via deamidation.

TABLE 13

Deamidation detected by RP-HPLC of peak B' species in formulations containing 0.2 mg/ml IL-2, 10 mM sodium succinate at pH 6, and 150 mM arginine, 150 mM NaCl, or 270 mM sorbitol.

| | % Peak B' (Deamidation) at t = 0 and 2 weeks | | | |
|---|---|---|---|---|
| Formulation | t = 0 | −70° C. | 40° C. | 50° C. |
| 10 mM NaSuc, 150 mM Arg, pH6 | 0 | 0 | 0 | 0 |
| 10 mM NaSuc, 150 mM NaCl, pH6 | 0 | 0 | 0 | 3 |
| 10 mM NaSuc, 270 mM Sorbitol, pH6 | 0 | 0 | 2 | 2 |

EXAMPLE 4

Effect of Freeze-thawing on IL-2 Stability

Freezing-induced protein damage is usually caused by three mechanisms: (1) the protein is conformationally unstable at cold temperatures (cold denaturation); (2) the protein is susceptible to denaturation on ice-water interface; (3) the protein is damaged by changes in salt concentration or pH shift upon freezing.

Figure 7:
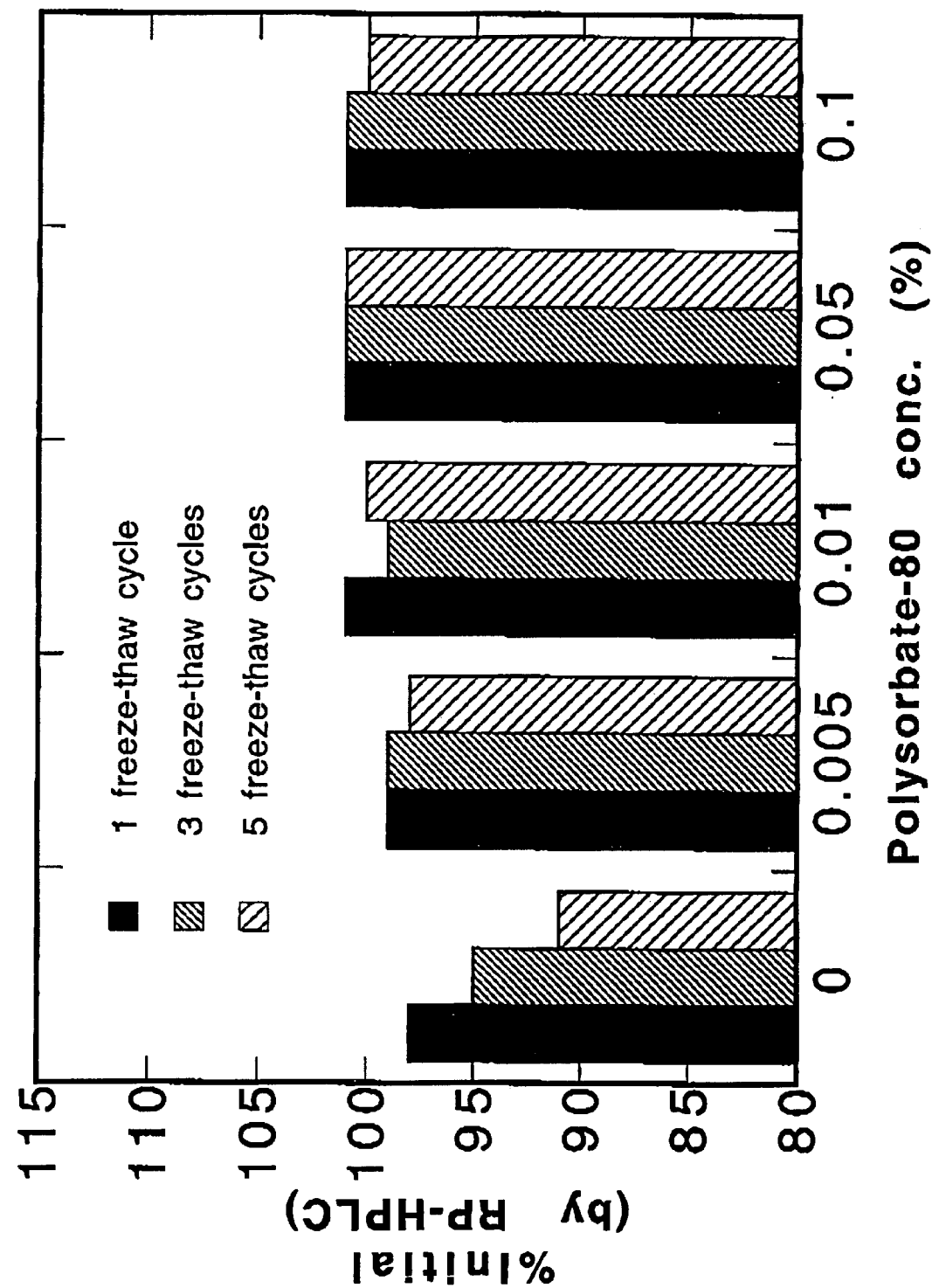
FIG. 7 shows the percent remaining of soluble IL-2, as analyzed by RP-HPLC, in samples treated with 1, 3, and 5 cycles of freeze-thaw from −70° C. to ambient temperature. Formulations contained 0.2 mg/ml IL-2, 10 mM sodium succinate at pH 6, 150 mM arginine, and 0 to 0.1% polysorbate 80.

In the case of IL-2, protein loss during freeze-thaws is probably caused by denaturation and aggregation on the ice-water interface since the nonionic surfactant polysorbate 80 effectively protected Il-2 from freeze-thaw damage. As shown in FIG. 7, the amount of soluble IL-2 decreases upon each cycle of freeze-thaw in a formulation containing 0.2 mg/ml IL-2, 10 mM sodium succinate at pH 6, and 150 mM arginine. The addition of polysorbate 80 in the formulation increases IL-2 stability against multiple freeze-thaws. When the concentration of polysorbate 80 reaches 0.05% and above, IL-2 is fully protected from freeze-thaw damage.

EXAMPLE 5

Effect of Mechanical Shearing on IL-2 Stability 5.1. Effect of Polysorbate 80, EDTA, Protein Concentration, and Fill Volume Studies were carried out to examine shear-stress-induced loss of soluble IL-2. Two types of shear stresses were assessed: shaking on an Orbital shaker (VWR Scientific, Cat. No. 57018-754) and vortexing on a vortexer (Fisher Scientific, model Genie 2, with the speed set at 4). Various IL-2 formulations were filled 1 ml in 3-cc vials. These vials were stored in a refrigerator (control samples), placed on a laboratory bench overnight (static samples), shaken at 200 RPM overnight (shaking samples), or vortexed one min (vortexing samples). Table 14 shows results of change in the amount of soluble IL-2 for these samples.

Compared with the refrigerated control samples, both static samples and shaking samples show no loss in IL-2. Thus, IL-2 is stable at ambient temperature and is stable to the shaking treatment. On the other hand, when these formulations were subjected to one min vortexing, various amounts of losses were detected. Formulations containing 0.1 to 0.5 mg/ml IL-2 or 1 and 5 mM EDTA or low concentrations of polysorbate 80 (0.005 to 0.05%) all show 25–50% loss of soluble IL-2. Therefore, one min vortexing was more detrimental than overnight shaking to IL-2 molecules. The loss of IL-2 could be prevented by increasing the concentration of polysorbate 80 in the formulation to equal to and greater than 0.1%. In addition, fully filled vials with no air left in the headspace also show minimal loss of soluble IL-2 upon one min vortexing, indicating that air-liquid interface was the major factor causing the damage.

TABLE 14

Change in the amount of soluble IL-2 for samples stored at ambient temperature overnight (Static), shaken at 200 RPM overnight (Shaking) and vortexed for 1 min (Vortexing) as compared with those stored at 4° C. The control formulation contained 0.2 mg/ml IL-2, 10 mM sodium succinate at pH 6, and 150 mM arginine. The formulation was filled 1 ml in 3 cc glass vials except for the completely filled sample, which had the control sample filled completely to the top of the 3 cc vials, leaving no air in the headspace. Soluble IL-2 was quantified by RP-HPLC.

| | % Remaining of soluble IL-2 | | |
|---|---|---|---|
| Sample (1 ml fill in 3 cc vials) | Static Overnight | Shaking Overnight | Vortexing 1 min |
| 0.2 mg/ml IL-2 (control) | 99.6 | 100.8 | 74.7 |
| 0.1 mg/ml IL-2 | 100.3 | 102.7 | 72.0 |
| 0.5 mg/ml IL-2 | 99.7 | 101.0 | 68.6 |
| 1 mM EDTA | 97.6 | 101.2 | 59.6 |
| 5 mM EDTA | 99.3 | 102.7 | 72.2 |
| 0.005% polysorbate 80 | 100.6 | 100.0 | 46.5 |
| 0.01% polysorbate 80 | 99.7 | 100.4 | 66.1 |
| 0.05% polysorbate 80 | 99.3 | 100.3 | 93.9 |
| 0.1% polysorbate 80 | 99.2 | 100.0 | 89.0 |
| 0.2% polysorbate 80 | 99.3 | 99.2 | 99.8 |
| 0.5% polysorbate 80 | 99.1 | 98.4 | 99.7 |
| 1 mM EDTA, 0.1% polysorbate 80 | 99.6 | 100.1 | 99.8 |
| Complete filled vials | 99.4 | 100.1 | 96.5 |

5.2 Effect of Arginine

The effect of arginine on IL-2 stability against vortexing damage is reported in Table 15. Increasing arginine concentration from 150 mM to 230 mM results in a 3% increase in the amount of soluble IL-2 from 65% to 69% after subjecting to one min vortexing. Thus, arginine has a minor effect on IL-2 against shear damage although it showed previously a great stabilization effect on IL-2 against degradation due to aggregate formation.

Effect of polysorbate 80 in the 230 mM arginine formulation was tested. Addition of a low concentration of polysorbate 80 (0.02%) destabilizes IL-2 and addition of a high concentration of polysorbate 80 (0.1%) stabilizes IL-2 against vortexing damage.

TABLE 15

Percent remaining of soluble IL-2 in various formulations upon 1 min vortexing as analyzed by RP-HPLC

| Formulation (all contains 0.5 mg/ml IL-2 except otherwise noted) | % IL-2 remaining |
|---|---|
| 150 mM Arginine, 10 mM NaSuc, 1 mM EDTA, pH 5.8 | 65.5 |
| 150 mM Arginine, 81 mM Suc acid, 1 mM EDTA, pH 5.8 | 65.3 |
| 230 mM Arginine, 10 mM NaSuc, 1 mM EDTA, pH 5.8 | 69.0 |
| 230 mM Arginine, 128 mM Suc acid, 1 mM EDTA, pH 5.8 | 68.9 |
| 230 mM Arginine, 128 mM Suc acid, 1 mM EDTA, 0.02% Tw 80, pH 5.8 | 55.1 |
| 230 mM Arginine, 128 mM Suc acid, 1 mM EDTA, 0.1% Tw 80, pH 5.8 | 99.5 |

5.3. Shipping Study

Figure 8:
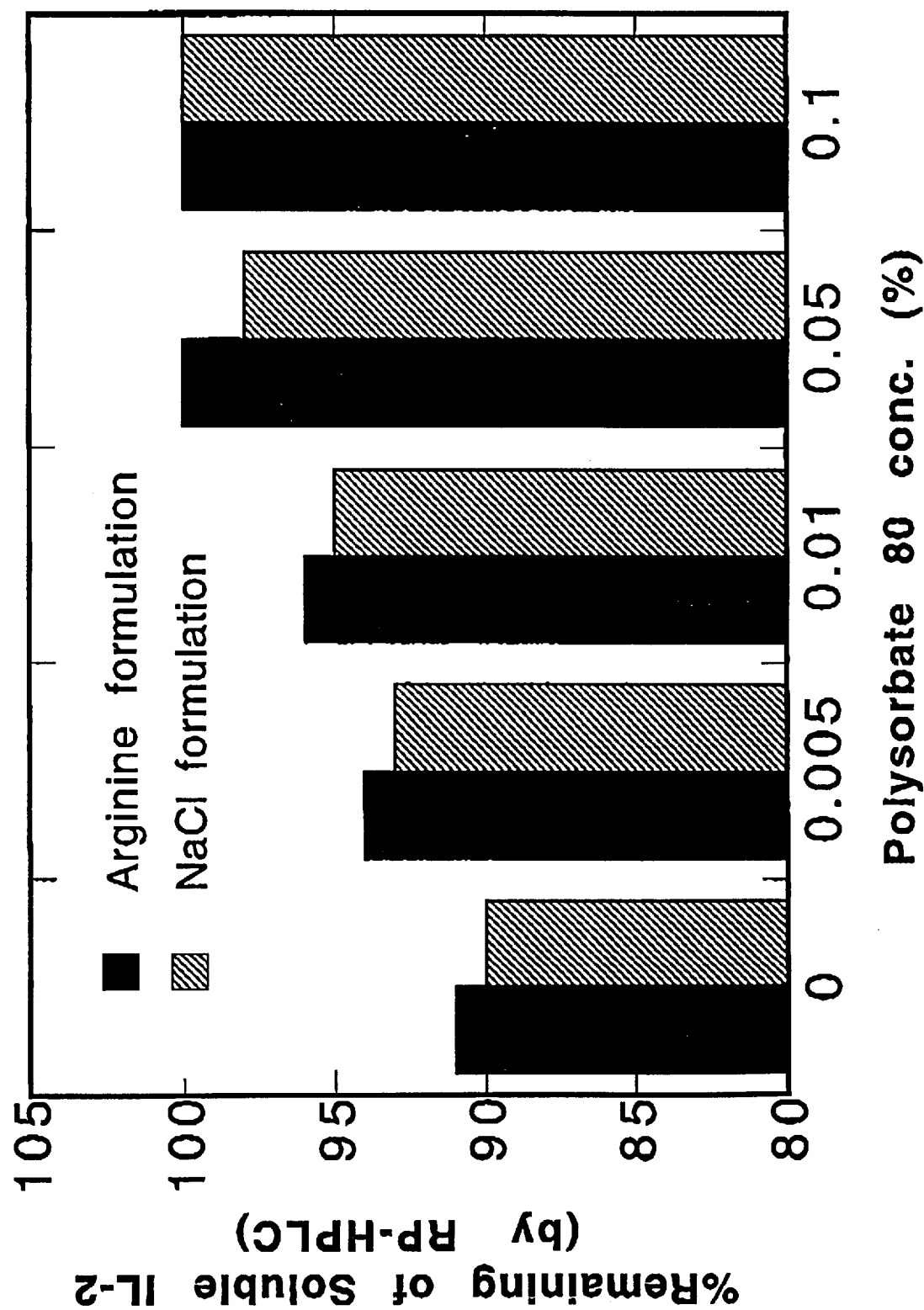
FIG. 8 shows the percent remaining of soluble IL-2, as analyzed by RP-HPLC, in samples treated with shipment from Emeryville, Calif., to St. Louis, Mo., and from St. Louis back to Emeryville on ice. Two formulations containing various amount of polysorbate 80 were used: an arginine formulation, containing 0.2 mg/ml IL-2 in 10 mM sodium succinate at pH 6 and 150 mM arginine; and a NaCl formulation, containing 0.2 mg/ml IL-2 in 10 mM sodium citrate at pH 6.5 and 200 mM NaCl.

Shear damage on IL-2 during product shipment was investigated in a real shipping study. IL-2 was prepared in an arginine formulation and a NaCl formulation, both with varying amounts of polysorbate 80. These IL-2 samples were shipped on ice by air from Emeryville, Calif., to St. Louis, Mo., and from St. Louis back to Emeryville. FIG. 8 shows RP-HPLC analysis of the amount of soluble IL-2 in these samples. Without the presence of polysorbate 80 in the formulation, about 10% loss of IL-2 is observed in both arginine and NaCl formulated samples. The stability differences between the arginine formulation and the NaCl formulation are negligible, around 1%. With the presence of polysorbate 80 in the formulation, loss of IL-2 is reduced. At 0.1% polysorbate 80, no loss is observed, indicating that IL-2 was fully protected at this surfactant concentration. Thus, 0.1% polysorbate 80 is effective in the formulation to prevent IL-2 from acute shear damage during shipping.

In conclusion, arginine may serve as a primary stabilizing agent in liquid IL-2 pharmaceutical formulations during long-term storage to decrease IL-2 aggregation and deamidation. To further increase arginine concentration in the formulation, and thus to achieve a greater IL-2 stability but still maintain the solution isotonicity, succinic acid is preferably used to titrate arginine base to pH 5.8. In addition, methionine and EDTA may be included in the formulation to prevent methionine oxidation of the protein. Finally, a nonionic surfactant, such as polysorbate 80, may be included in the formulation to prevent IL-2 from damage by freeze-thawing and mechanical shearing.

EXAMPLE 6

Preservative Effectiveness Test

Several formulations containing antimicrobial preservatives have been subjected to a United States Pharmacopoeia (USP) preservative efficacy test. The results are presented in Table 16. The control sample without preservative failed the test while all formulations containing a preservative passed the test.

TABLE 16

USP preservative efficacy test for rhIL-2 formulations. The control formulation contained 0.1 mg/ml rhIL-2, 230 mM L-arginine base, 128 mM succinic acid, 1 mM EDTA, 5 mM methionine, 0.1% polysorbate 80, at a pH of 5.8.

| PRESERVATIVE | USP TEST |
| --- | --- |
| Control | fail |
| 0.9% benzyl alcohol | pass |
| 1.3% benzyl alcohol | pass |
| 1.7% benzyl alcohol | pass |
| 0.5% chlorobutanol | pass |
| 0.5% phenol | pass |

EXAMPLE 7

Pain Producing Properties

A rat model developed at University of Florida, College of Dentistry, OMSDS Division of Neuroscience, was used to assess pain-producing properties, more particularly the burning and stinging pain produced by formulations. The model is based on an assay of the current induced in sensory cells that carry pain messages. To conduct the assay, sensory cells (rat dorsal root ganglion) are isolated in a recording chamber. Recordings are made from individual cells that are pre-selected based upon nociceptive (pain-inducing) criteria. Burning pain, stinging pain, and standardized pain scores are computer for the tested formulation. A burning pain score is defined by the response to the test formulation relative to capsaicin (500 nM). Capsaicin is well known for its capacity to produce intense burning pain in humans (Cooper et al. (1986) *Pain* 24:93–116). A stinging pain score is computed as the ratio of the current produced by the test formulation to that produced by a solution buffered to pH 5.0. The standardized pain score rates the formulation relative to normal saline (0.9% NaCl, non-buffered), a common hospital pharmacy parenteral that is known to produce a stinging sensation.

A liquid L-arginine base-succinic acid formulation has been subjected to the pain analysis via this model. Results of these two test solutions are shown in Table 17. Based upon scores calculated for burning pain, stinging pain, and the standardized pain score, the L-arginine-succinic acid formulation exhibited excellent properties in comparison with normal saline. It was also observed that the test current diminished during the application of the formulation (time-dependent decrease) while it did not diminish with normal saline. This demonstrates that this formulation is better tolerated than saline as evaluated by this assay.

TABLE 17

Burning, stinging, and standardized pain scores for the liquid formulation and 0.9% NaCl. The liquid formulation contained 230 mM L-arginine base, 128 mM succinic acid, 1 mM EDTA, 5 mM methionine, 0.1% polysorbate 80, at a pH of 5.8.

| Formulation | Burning Pain | Stinging Pain | Standardized pain score |
| --- | --- | --- | --- |
| 0.9% NaCl | 0.084 ± 0.006 | 2.44 ± 0.62 | 1.73 ± 0.73 |
| RrhIL-2 liquid formulation | 0.044 ± 0.019 | 0.65 ± 0.23 | 0.16 ± 0.05 |

EXAMPLE 8

Stability Studies with TFPI

Stability and solubility studies of TFPI in various formulations have demonstrated that L-arginine is a stabilizer (data not shown) to TFPI and charged buffer species such as citrate ions have a more profound solubilizing effect. In this study, the effects of L-arginine concentration and buffering system on TFPI stability in various formulations were examined. In particular, the influence of buffering system in the form of an acid substantially free of its salt farm versus a mixture of an acid and its salt form were tested as previously noted for IL-2 formulations in the foregoing examples.

Materials and Methods

A TFPI solution was formulated to 0.6 mg/ml in 20 mM sodium citrate and 300 mM L-arginine at pH 5.5. This solution was buffer exchanged via dialysis at 4° C. using the Spectral Por #7 membranes (MWCO 3,500, ID# 132–110) to various L-arginine formulations buffered to pH 6.5 by either citrate or succinate buffering system. Following dialysis, the TFPI concentration of each solution was measured using UV/Vis spectroscopy. Each solution was then diluted down to 0.15 mg/ml using the appropriate buffer. The prepared solutions were then aliquoted (1 ml each) to 3-cc vials for stability storage. Enough vials were set aside at this point for the T=0 time point. The rest of the vials were placed in a 50° C. incubator for an accelerated stability study. Time points were then taken at 3, 7, 14, and 30 days. For analysis at each time point, the contents of each vial were transferred to a 1.7 ml microcentrifuge tube and then centrifuged at 10K rpm for approximately 2 minutes. The centrifuged supernatant of the samples was taken from this tube for analysis using IEX-HPLC (description needed), which was known from previous studies to be a stability indicating assay.

Results and Discussion

TFPI was formulated to 0.15 mg/ml final concentration in various formulations containing either L-arginine base or L-arginine HCl. L-arginine HCl formulations were buffered to pH 5.5 by 10 mM citric acid or succinic acid in combination with its respective conjugate sodium salt. L-arginine base formulations were titrated to pH 5.5 by either citric acid or succinic acid. A total of eight studies were carried out as listed below:

1) 20–150 mM L-arginine HCl buffered to pH 5.5 by 10 mM citric acid and sodium citrate;
2) 20–150 mM L-arginine base titrated to pH 5.5 by citric acid;
3) 100–300 mM L-arginine HCl buffered to pH 5.5 by 10 mM citric acid and sodium citrate;
4) 100–300 mM L-arginine base titrated to pH 5.5 by citric acid;
5) 20–150 mM L-arginine HCl buffered to pH 5.5 by 10 mM succinic acid and sodium succinate;
6) 20–150 mM L-arginine base titrated to pH 5.5 by succinic acid;
7) 100–300 mM L-arginine HCl buffered to pH 5.5 by 10 mM succinic acid and sodium succinate; and
8) 100–300 mM L-arginine base titrated to pH 5.5 by succinic acid.

The major degradation pathway for TFPI was previously determined to be protein aggregation/precipitation (Chen et al. (1999) *J. Pharm. Sci.* 88:881–888). TFPI degradation can be followed by monitoring the remaining soluble protein in stability samples. TFPI solutions formulated at different L-arginine concentrations were stored at 50° C. for an accelerated stability study. Samples were taken at predetermined time intervals. Soluble protein in the samples was separated from aggregated/precipitated protein through centrifugation in a microcentrifuge tube. The amount of soluble protein was determined by the IEX-HPLC method (Chen et al. (1999) *J. Pharm. Sci.* 88:881–888). The data were then fitted as a function of storage time by a single exponential kinetic equation (Y=YoEXP(-k1t) to calculate the half-life for the remaining soluble protein using the KaleidaGraph graphic software (Synergy Software, Reading Pa.).

Figure 9:
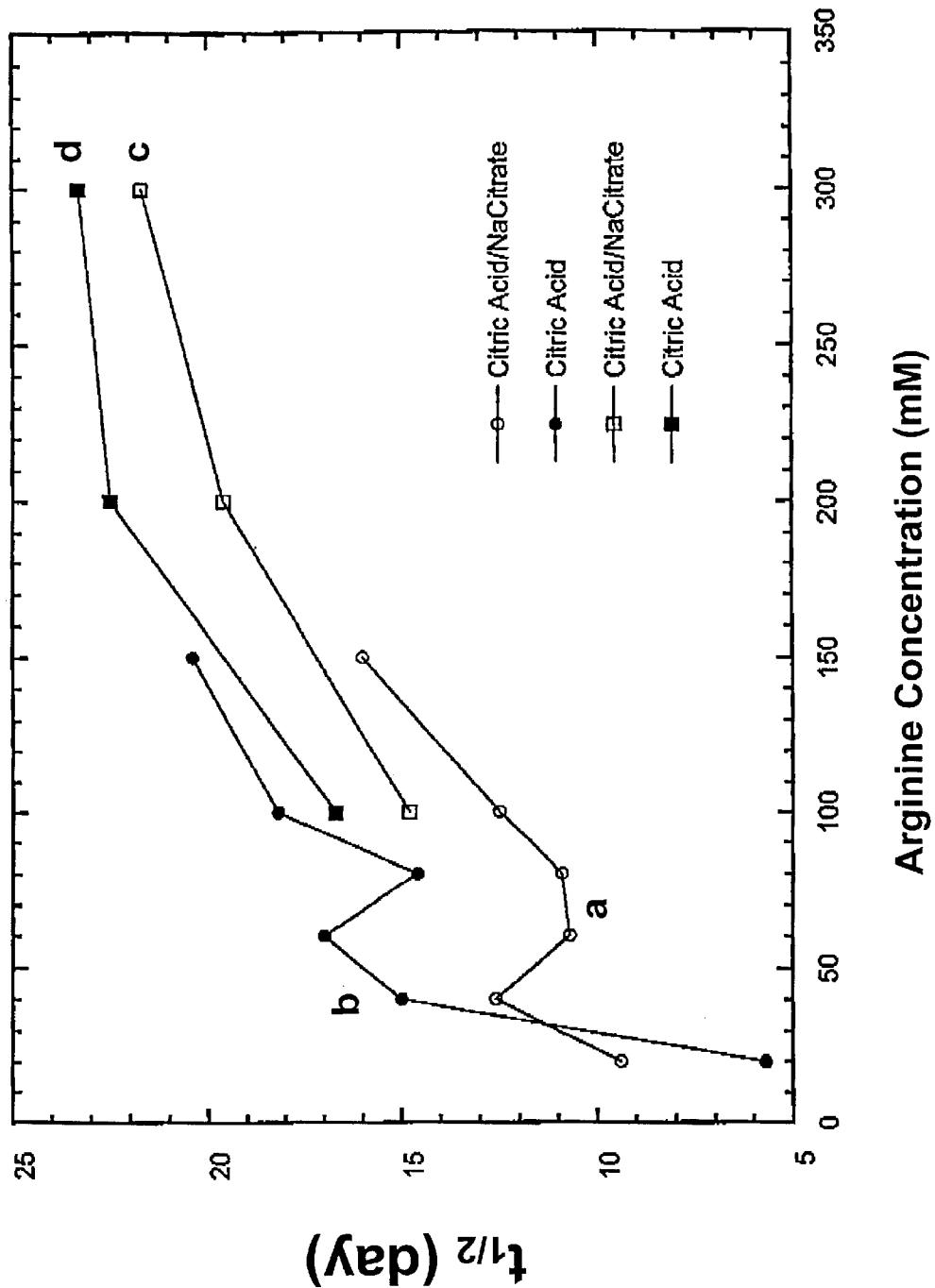
FIG. 9 shows the half-life ($t_{1/2}$, in days) of remaining soluble TFPI in four formulations analyzed by IEX-HPLC as a function of arginine concentration at 50° C. All formulations contained 0.15 mg/ml TFPI and either L-arginine base or L-arginine HCl, buffered to pH 5.5 with either citric acid or 10 mM citric acid and sodium citrate. The specific TFPI formulations contained: (a) 20–150 mM L-arginine HCl, 10 mM citric acid and sodium citrate as buffer; (b) 20–150 mM L-arginine base, titrated with citric acid; (c) 100–300 mM L-arginine HCl, 10 mM citric acid and sodium citrate as buffer; (d) 100–300 mM L-arginine base titrated with citric acid.

The half-life ($t_{1/2}$) values for the remaining soluble TFPI for the formulations buffered by citrate addition of or sodium citrate are shown in Table 18. Those for the formulations buffered by succinic acid or sodium succinate are shown in Table 19. These data demonstrate that the half-life value increases with increasing L-arginine concentration in these formulations. These data are also plotted in FIGS. 9 and 10 for citrate and succinate buffer systems, respectively. The half-life value plots as a parabolic curve and increases as a function of arginine concentration. This establishes that L-arginine is a stabilizer for TFPI.

Figure 10:
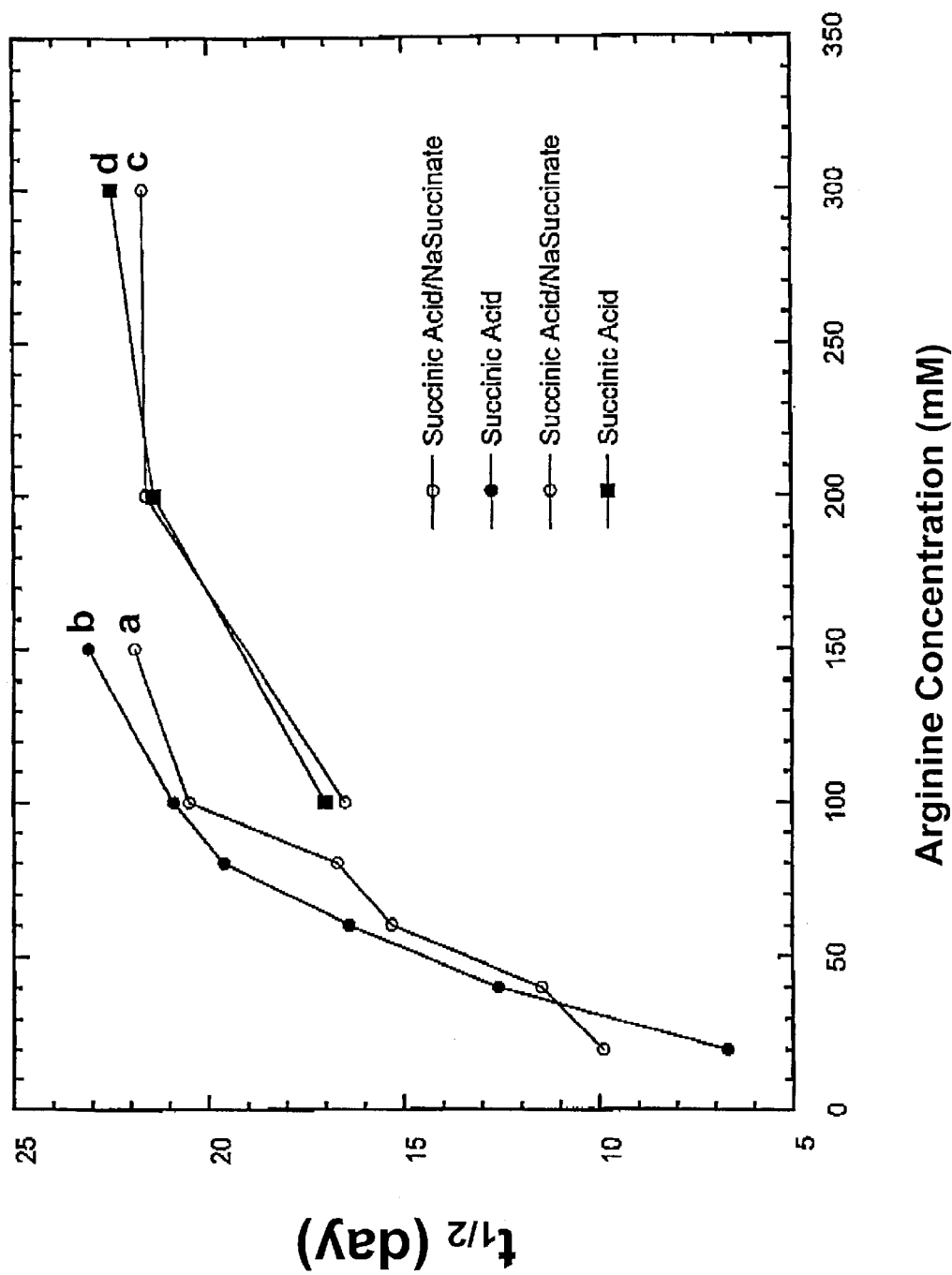
FIG. 10 shows the half-life ($t_{1/2}$, in days) of remaining soluble TFPI in four formulations analyzed by IEX-HPLC as a function of arginine concentration at 50° C. All formulations contained 0.15 mg/ml TFPI and either L-arginine base or L-arginine HCl, buffered to pH 5.5 with either succinic acid or 10 mM succinic acid and sodium succinate. The specific TFPI formulations contained: (a) 20–150 mM L-arginine HCl, 10 mM succinic acid and sodium succinate as buffer; (b) 20–150 mM L-arginine base, titrated with succinic acid; (c) 100–300 mM L-arginine HCl, 10 mM succinic acid and sodium succinate as buffer; and (d) 100–300 mM L-arginine base titrated with succinic acid.
Figure 11:
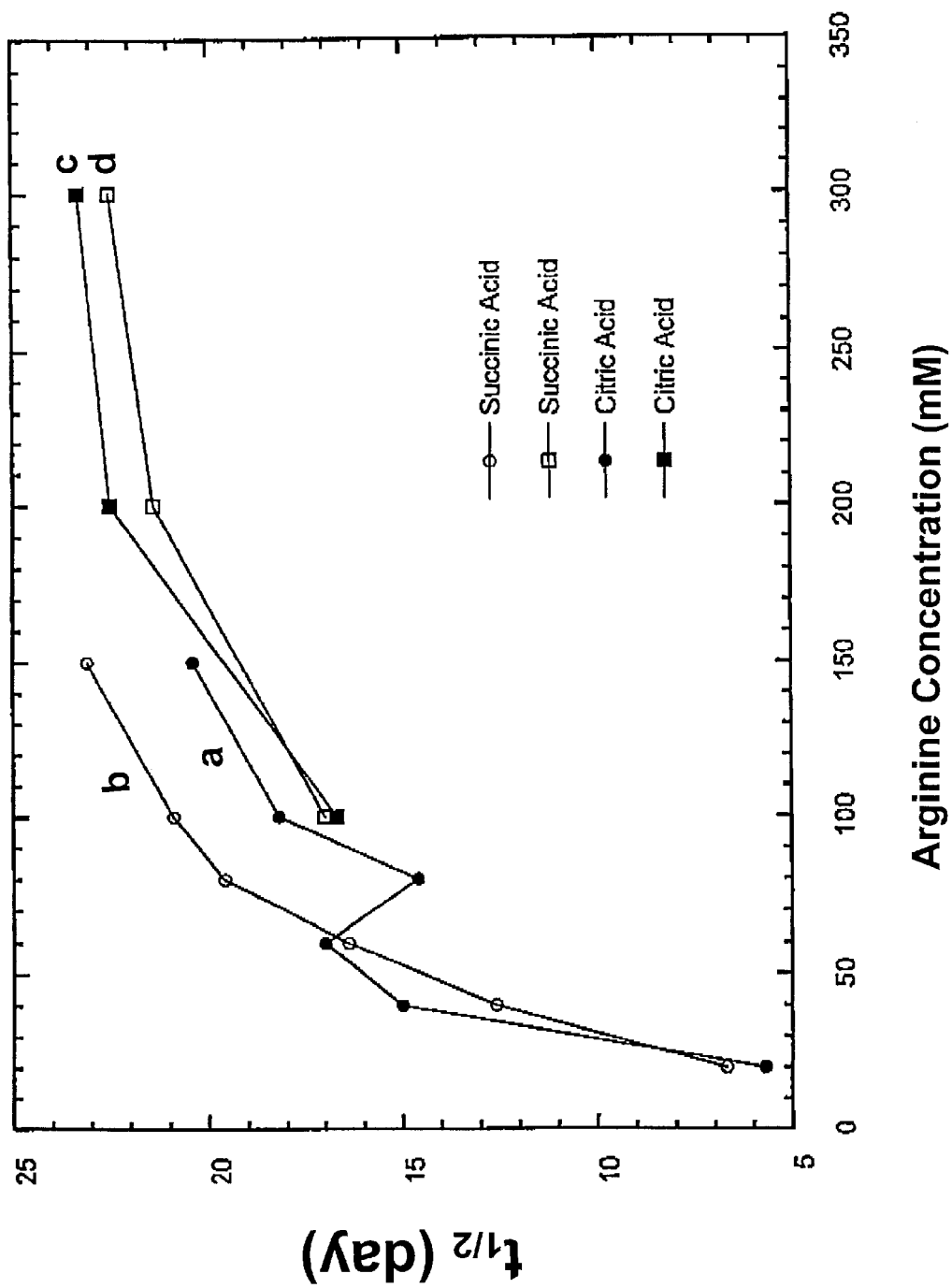
FIG. 11 shows the half-life ($t_{1/2}$, in days) of remaining soluble TFPI in four formulations analyzed by IEX-HPLC as a function of arginine concentration at 50° C. All formulations contained 0.15 mg/ml TFPI and L-arginine base, titrated to pH 5.5 with either succinic acid or citric acid. The specific TFPI formulations contained: (a) 20–150 mM L-arginine base, titrated with citric acid; (b) 20–150 mM L-arginine base, titrated with succinic acid; (c) 100–300 mM L-arginine base titrated with citric acid; (d) 100–300 mM L-arginine base titrated with succinic acid.

Between the two buffering systems, the difference in TFPI stability appears negligible. Although the citrate buffering system showed more variability (FIG. 9), the two half-life vs. arginine concentration curves for the succinate buffering system were essentially superimposable (FIG. 10). TFPI achieved similar stability at similar L-arginine concentration regardless of which of the buffering systems was used for pH adjustment. FIG. 11 also compares the half-life vs. arginine concentration curves between the succinic acid buffer system and the citric acid system. This figure shows that there is no major difference in TFPI stability as long as the arginine concentration remains the same in the formulation. These data demonstrate that the stabilizing effect was mainly contributed from the arginine.

However, acid titration with either succinic or citric acid, allows for a greater concentration of arginine in the formulation (and hence increased stability) while maintaining isotonicity. Thus, for example, both formulations 3-3 and 4-3 in Table 18 have 300 mM L-arginine in the formulations and their half-life values are similar. However, the 3-3 formulation used 10 mM citric acid and sodium citrate to buffer 300 mM L-arginine HCl to pH 5.5 and had a solution osmolarity of 497 mOsm/kg. This is a hypertonic formulation and is not preferred as an injectable formulation. On the other hand, the 4-3 formulation used 121 mM citric acid in combination with 300 mM L-arginine base to adjust pH to 5.5 and had a solution osmolarity of 295 mOsm/kg. This formulation is very close to an isotonic solution (290 mmol/kg), and thus is a more preferred injectable formulation. If a conventional way for pH adjustment were used, for instance, with 10 mM citric acid and sodium citrate, one could only add slightly more than 150 mM L-arginine to the formulation without exceeding isotonicity. The half-life of the 150 mM L-arginine formulation (Code 1-6) is 16 days in comparison with 23 days for the 300 mM L-arginine formulation (Code 4-3). Therefore, formulating TFPI with an acid base (i.e., arginine-base) as a stabilizer and a buffer comprising an acid substantially free of its salt form (i.e., succinic acid) provides an effective means to add more stabilizer (i.e., arginine) to maximize stabilizing effect on TFPI.

CONCLUSION

This example demonstrates that L-arginine stabilizes TFPI by extending its storage shelf-life. By using acid titration, one can add more arginine to the formulation to maximize the stabilizing effect without exceeding isotonicity, which is preferred for injectable formulations.

TABLE 18

Stability data for TFPI arginine-citrate pH 5.5 formulations. The half-life ($t_½$) was obtained by fitting 50° C. stability data using a single exponential kinetic equation.

| Code | Formulation | Osmolarity (mmol/kg) | $t_½$ (Day) |
|---|---|---|---|
| 1-1 | 20 mM L-Arg HCl, 10 mM Citric acid/Na Citrate | 66 | 9.4 |
| 1-2 | 40 mM L-Arg HCl, 10 mM Citric acid/Na Citrate | 81 | 12.6 |
| 1-3 | 60 mM L-Arg HCl, 10 mM Citric acid/Na Citrate | 91 | 10.7 |
| 1-4 | 80 mM L-Arg HCl, 10 mM Citric acid/Na Citrate | 106 | 10.9 |
| 1-5 | 100 mM L-Arg HCl, 10 mM Citric acid/Na Citrate | 190 | 12.5 |
| 1-6 | 150 mM L-Arg HCl, 10 mM Citric acid/Na Citrate | 276 | 16.0 |
| 2-1 | 20 mM L-Arg Base titrated by 8.9 mM Citric acid | 67 | 5.7 |
| 2-2 | 40 mM L-Arg Base titrated by 17.8 mM Citric acid | 84 | 15.0 |

TABLE 18-continued

Stability data for TFPI arginine-citrate pH 5.5 formulations. The half-life ($t_{1/2}$) was obtained by fitting 50° C. stability data using a single exponential kinetic equation.

| Code | Formulation | Osmolarity (mmol/kg) | $t_{1/2}$ (Day) |
|---|---|---|---|
| 2-3 | 60 mM L-Arg Base titrated by 26.6 mM Citric acid | 95 | 17.0 |
| 2-4 | 80 mM L-Arg Base titrated by 34.2 mM Citric acid | 109 | 14.6 |
| 2-5 | 100 mM L-Arg Base titrated by 42.6 mM Citric acid | 119 | 18.2 |
| 2-6 | 150 mM L-Arg Base titrated by 62.4 mM Citric acid | 147 | 20.4 |
| 3-1 | 100 mM L-Arg HCl, 10 mM Citric acid/Na Citrate | 239 | 14.8 |
| 3-2 | 200 mm L-Arg HCl, 10 mM Citric acid/Na Citrate | 358 | 19.6 |
| 3-3 | 300 mM L-Arg HCl, 10 mM Citric acid/Na Citrate | 497 | 21.7 |
| 4-1 | 100 mM L-Arg Base titrated by 42.2 mM Citric acid | 155 | 16.7 |
| 4-2 | 200 mM L-Arg Base titrated by 81.8 mM Citric acid | 224 | 22.5 |
| 4-3 | 300 mM L-Arg Base titrated by 121 mM Citric acid | 295 | 23.3 |

TABLE 19

Stability data for TFPI arginine-succinate pH 5.5 formulations. The half-life ($t_{1/2}$) was obtained by fitting 50° C. stability data using a single exponential kinetic equation.

| Code | Formulation | Osmolarity (mmol/kg) | $t_{1/2}$ (Day) |
|---|---|---|---|
| 1-1 | 20 mM L-arg HCl, 10 mM Succinic acid/Na Succinate | 66 | 9.9 |
| 1-2 | 40 mM L-arg HCl, 10 mM Succinic acid/Na Succinate | 97 | 11.5 |
| 1-3 | 60 mM L-arg HCl, 10 mM Succinic acid/Na Succinate | 129 | 15.3 |
| 1-4 | 80 mM L-arg HCl, 10 mM Succinic acid/Na Succinate | 163 | 16.7 |
| 1-5 | 100 mM L-arg HCl, 10 mM Succinic acid/Na Succinate | 197 | 20.5 |
| 1-6 | 150 mM L-arg HCl, 10 mM Succinic acid/Na Succinate | 282 | 21.9 |
| 2-1 | 20 mM L-arg Base titrated by 12.5 mM Succinic acid | 40 | 6.7 |
| 2-2 | 40 mM L-arg Base titrated by 25.2 mM Succinic acid | 62 | 12.6 |
| 2-3 | 60 mM L-arg Base titrated by 37.5 mM Succinic acid | 85 | 16.4 |
| 2-4 | 80 mM L-arg Base titrated by 49.9 mM Succinic acid | 107 | 19.6 |
| 2-5 | 100 mM L-arg Base titrated by 62.4 mM Succinic acid | 129 | 20.9 |
| 2-6 | 150 mM L-arg Base titrated by 91.4 mM Succinic acid | 192 | 23.1 |
| 3-1 | 100 mM L-arg HCl, 10 mM Succinic acid/Na Succinate | 207 | 16.5 |
| 3-2 | 200 mM L-arg HCl, 10 mM Succinic acid/Na Succinate | 353 | 21.6 |
| 3-3 | 300 mM L-arg HCl, 10 mM Succinic acid/Na Succinate | 515 | 21.7 |
| 4-1 | 100 mM L-arg Base titrated by 61.3 mM Succinic acid | 127 | 17.0 |
| 4-2 | 200 mM L-arg Base titrated by 122 mM Succinic acid | 256 | 21.4 |
| 4-3 | 300 mM L-arg Base titrated by 180 mM Succinic acid | 363 | 22.5 |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A stabilized liquid pharmaceutical composition comprising interleukin-2 (IL-2) or variant thereof as a therapeutically active component, a stabilizing agent, and a buffering agent, wherein the stabilizing agent is arginine in its free base form and the buffering agent is succinic acid substantially free of its salt form, wherein said arginine in its free base form is present in said composition at a concentration of about 150 mM to about 350 mM and said succinic acid is present in said composition at a concentration of about 80 mM to about 190 mM, and wherein said variant thereof has at least 70% sequence identity with said IL-2.

2. The composition of claim 1, wherein said arginine in its free base form is present in said composition at a concentration of about 230 mM and said succinic acid is present at a concentration of about 128 mM, wherein said composition has a pH of about 5.0 to about 6.5 and an osmolarity of about 250 mmol/kg to about 330 mmol/kg.

3. The composition of claim 1, wherein said variant thereof has at least 80% sequence identity with said IL-2.

4. The composition of claim 3, wherein said variant thereof has at least 90% sequence identity with said IL-2.

5. The composition of claim 4, wherein said variant thereof has at least 95% sequence identity with said IL-2.

6. A stabilized liquid pharmaceutical composition comprising tissue factor pathway inhibitor (TFPI) or variant thereof as a therapeutically active component, a stabilizing agent, and a buffering agent, wherein the stabilizing agent is arginine in its free base form and the buffering agent is succinic acid substantially free of its salt form, wherein said arginine in its free base form is present in said composition at a concentration of about 175 mM to about 325 mM and said succinic acid is present in said composition at a concentration of about 80 mM to about 190 mM, and wherein said variant thereof has at least 70% sequence identity with said TFPI.

7. The composition of claim 6, wherein said arginine in its free base form is present in said composition at a concentration of about 200 mM to about 300 mM and said succinic acid is present at a concentration of about 120 mM to about 180 mM, wherein said composition has a pH of about 5.0 to about 6.5 and an osmolarity of about 240 mmol/kg to about 360 mmol/kg.

8. The composition of claim 6, wherein said variant thereof has at least 80% sequence identity with said TFPI.

9. The composition of claim 8, wherein said variant thereof has at least 90% sequence identity with said TFPI.

10. The composition of claim 9, wherein said variant thereof has at least 95% sequence identity with said TFPI.

11. A stabilized liquid pharmaceutical composition comprising tissue factor pathway inhibitor (TFPI) or variant thereof as a therapeutically active component, a stabilizing agent, and a buffering agent, wherein the stabilizing agent is arginine in its free base form and the buffering agent is citric acid substantially free of its salt form, wherein said arginine in its free base form is present in said composition at a concentration of about 175 mM to about 400 mM and said citric acid is present in said composition at a concentration of about 40 mM to about 200 mM, and wherein said variant thereof has at least 70% sequence identity with said TFPI.

12. The composition of claim 11, wherein said arginine in its free base form is present in said composition at a concentration of about 250 mM to about 350 mM and said citric acid is present at a concentration of about 100 mM to about 150 mM, wherein said composition has a pH of about 5.0 to about 6.5 and an osmolarity of about 240 mmol/kg to about 360 mmol/kg.

13. The composition of claim 11, wherein said variant thereof has at least 80% sequence identity with said TFPI.

14. The composition of claim 13, wherein said variant thereof has at least 90% sequence identity with said TFPI.

15. The composition of claim 14, wherein said variant thereof has at least 95% sequence identity with said TFPI.

16. A stabilized liquid pharmaceutical composition comprising:
   a) a polypeptide or variant thereof as a therapeutically active component, said variant having at least 70% sequence identity with said polypeptide;
   b) a stabilizing agent, wherein said stabilizing agent is an amino acid base in its free base form, said amino acid base being selected from a group consisting of arginine, lysine, and a mixture of arginine and lysine, wherein said amino acid base is present in an amount sufficient to decrease aggregate formation of said polypeptide or variant thereof during storage of said composition relative to aggregate formation of said polypeptide or variant thereof during storage of said composition in the absence of said amino acid base in said composition; and
   c) a buffering agent, wherein said buffering agent is an acid substantially free of its salt form;
said polypeptide being selected from the group consisting of interleukin-2 (IL-2), tissue factor pathway inhibitor (TFPI), and β-interferon (IFN-β).

17. The composition of claim 16, further comprising methionine in an amount sufficient to inhibit oxidation of at least one methionine residue in said polypeptide or variant thereof during storage of said composition.

18. The composition of claim 16 further comprising a nonionic surfactant in an amount sufficient to inhibit aggregation of said polypeptide or variant thereof in response to freeze-thawing or mechanical shearing during storage of said composition.

19. The composition of claim 18, wherein said nonionic surfactant is polysorbate 80.

20. A dried form of the composition of claim 16, wherein said dried form is selected from the group consisting of a lyophilized form and a spray-dried form.

21. The composition of claim 16, wherein said composition has an osmolarity of about 240 mmol/kg to about 360 mmol/kg.

22. The composition of claim 16, wherein said composition has a pH within a range of about pH 4.0 to about pH 9.0.

23. The composition of claim 16, wherein said acid is selected from the group consisting of acetic acid, aspartic acid, succinic acid, citric acid, phosphoric acid, and glutamic acid.

24. The composition of claim 23, wherein said acid is succinic acid.

25. The composition of claim 24, wherein said amino acid base is arginine in its free base form present at a concentration of about 100 mM to about 400 mM and wherein said succinic acid is present in said composition within a concentration range of about 80 mM to about 190 mM.

26. The composition of claim 25, wherein said polypeptide is IL-2 or said variant thereof and said arginine in its free base form is present at a concentration of about 150 mM to about 350 mM.

27. The composition of claim 26, wherein said arginine in its free base form is present at a concentration of about 230 mM and wherein said succinic acid is present at a concentration of about 128 mM.

28. The composition of claim 27, wherein said IL-2 is recombinant human IL-2 (rhIL-2) or variant thereof having at least 70% sequence identity with human IL-2.

29. The composition of claim 28, wherein said composition has a pH of about 5.0 to about 6.5 and an osmolarity of about 250 mmol/kg to about 330 mmol/kg.

30. The composition of claim 25, wherein said polypeptide is tissue factor pathway inhibitor (TFPI) or said variant thereof and said arginine in its free base form is present at a concentration of about 175 mM to about 325 mM.

31. The composition of claim 30, wherein said arginine in its free base form is present at a concentration of about 200 mM to about 300 mM and wherein said succinic acid is present at a concentration of about 120 mM to about 180 mM.

32. The composition of claim 31, wherein said TFPI is recombinant human TFPI or variant thereof having at least 70% sequence identity with human TFPI.

33. The composition of claim 31, wherein said composition has a pH of about 5.0 to about 6.5 and an osmolarity of about 240 mmol/kg to about 360 mmol/kg.

34. The composition of claim 23, wherein said acid is citric acid.

35. The composition of claim 34, wherein said amino acid base is arginine in its free base form present at a concentration of about 175 mM to about 400 mM and wherein said citric acid is present in said composition within a concentration range of about 40 mM to about 200 mM.

36. The composition of claim 35, wherein said polypeptide is TFPI or said variant thereof.

37. The composition of claim 36, wherein said TFPI is recombinant human TFPI (rhTFPI) or variant thereof having at least 70% sequence identity with human TFPI.

38. The composition of claim 36, wherein said arginine in its free base form is present at a concentration of about 250 mM to about 350 mM and said citric acid is present at a concentration of about 100 mM to about 150 mM.

39. The composition of claim 38, wherein said composition has a pH of about 5.0 to about 6.5 and an osmolarity of about 240 mmol/kg to about 360 mmol/kg.

40. The composition of claim 16, wherein said variant thereof has at least 80% sequence identity with said polypeptide.

41. The composition of claim 40, wherein said variant thereof has at least 90% sequence identity with said polypeptide.

42. The composition of claim 41, wherein said variant thereof has at least 95% sequence identity with said polypeptide.

43. A method for increasing stability of a polypeptide or variant thereof that is a therapeutically active component in a liquid pharmaceutical composition, said variant thereof having at least 70% sequence identity with said polypeptide, said method comprising incorporating into said composition a stabilizing agent and a buffering agent, wherein said stabilizing agent is an amino acid base in its free base form, said amino acid base being selected from a group consisting of arginine, lysine, and a mixture of arginine and lysine, and said buffering agent is an acid substantially free of its salt form, wherein said amino acid base is present in an amount sufficient to decrease aggregate formation of said polypeptide or variant thereof during storage of said composition relative to aggregate formation of said polypeptide or variant thereof during storage of said composition in the absence of said amino acid base in said composition, said polypeptide being selected from a group consisting of interleukin-2 (IL-2), tissue factor pathway inhibitor (TFPI), and β-interferon (IFN-β).

44. The method of claim 43, wherein said composition has an osmolarity of about 240 mmol/kg to about 360 mmol/kg.

45. The method of claim 43, wherein said composition has a pH within a range of about pH 4.0 to about pH 9.0.

46. The method of claim 43, wherein said acid is selected from the group consisting of acetic acid, aspartic acid, succinic acid, citric acid, phosphoric acid, and glutamic acid.

47. The method of claim 46, wherein said acid is succinic acid.

48. The method of claim 43, wherein said variant thereof has at least 80% sequence identity with said polypeptide.

49. The method of claim 48, wherein said variant thereof has at least 90% sequence identity with said polypeptide.

50. The method of claim 49, wherein said variant thereof has at least 95% sequence identity with said polypeptide.

51. A method for increasing storage stability of a liquid pharmaceutical composition comprising a polypeptide or variant thereof as a therapeutically active component, said variant thereof having at least 70% sequence identity with said polypeptide, said method comprising incorporating into said composition a stabilizing agent and a buffering agent, wherein said stabilizing agent is an amino acid base in its free base form, said amino acid base being selected from a group consisting of arginine, lysine, and a mixture of arginine and lysine, and said buffering agent is an acid substantially free of its salt form, wherein said amino acid base is present in an amount sufficient to decrease aggregate formation of said polypeptide or variant thereof during storage of said composition relative to aggregate formation of said polypeptide or variant thereof during storage of said composition in the absence of said amino acid base in said composition, said polypeptide being selected from a group consisting of interleukin-2 (IL-2), tissue factor pathway inhibitor (TFPI), and β-interferon (IFN-β).

52. The method of claim 51, wherein said composition has an osmolarity of about 240 mmol/kg to about 360 mmol/kg.

53. The method of claim 51, wherein said composition has a pH within a range of about pH 4.0 to about pH 9.0.

54. The method of claim 51, wherein said acid is selected from the group consisting of acetic acid, aspartic acid, succinic acid, citric acid, phosphoric acid, and glutamic acid.

55. The method of claim 51, wherein said acid is succinic acid.

56. The method of claim 51, wherein said variant thereof has at least 80% sequence identity with said polypeptide.

57. The method of claim 56, wherein said variant thereof has at least 90% sequence identity with said polypeptide.

58. The method of claim 57, wherein said variant thereof has at least 95% sequence identity with said polypeptide.

* * * * *

UNITED STATES PATENT AND TRADEMARK OFFICE
CERTIFICATE OF CORRECTION

PATENT NO.      : 6,525,102 B1                                                     Page 1 of 1
DATED           : February 25, 2003
INVENTOR(S)     : Chen et al.

It is certified that error appears in the above-identified patent and that said Letters Patent is hereby corrected as shown below:

<u>Column 32,</u>
Line 30, Table 12, in the last sub-heading, "2 months" should read -- 12 months --.

Signed and Sealed this

Twelfth Day of August, 2003

JAMES E. ROGAN
*Director of the United States Patent and Trademark Office*